United States Patent
Zimmerman et al.

(10) Patent No.: US 8,993,509 B2
(45) Date of Patent: Mar. 31, 2015

(54) METHOD FOR TREATMENT OF CACHEXIA BY ADMINISTERING INHIBITORS OF ADIPOSE TRIGLYCERIDE LIPASE EXPRESSION OR ACTIVITY

(76) Inventors: Robert Zimmerman, Graz (AT); Rudolf Zechner, Graz (AT); Günther Haemmerle, Graz (AT); Gerald Höfler, Stattegg (AT); Suman Das, Graz (AT); Achim Lass, Graz (AT)

( * ) Notice: Subject to any disclaimer, the term of this patent is extended or adjusted under 35 U.S.C. 154(b) by 361 days.

(21) Appl. No.: 13/262,094

(22) PCT Filed: Mar. 31, 2010

(86) PCT No.: PCT/EP2010/054363
§ 371 (c)(1), (2), (4) Date: May 18, 2012

(87) PCT Pub. No.: WO2010/115825
PCT Pub. Date: Oct. 14, 2010

(65) Prior Publication Data
US 2012/0230943 A1   Sep. 13, 2012

Related U.S. Application Data

(60) Provisional application No. 61/211,604, filed on Mar. 31, 2010.

(51) Int. Cl.
*A01N 61/00* (2006.01)
*A61K 31/00* (2006.01)
(Continued)

(52) U.S. Cl.
CPC . *C12Q 1/44* (2013.01); *A61K 31/41* (2013.01); *A61K 31/495* (2013.01);
(Continued)

(58) Field of Classification Search
None
See application file for complete search history.

(56) References Cited

U.S. PATENT DOCUMENTS

| | | | |
|---|---|---|---|
| 6,143,780 | A | 11/2000 | Brouwer et al. |
| 2005/0143409 | A1 | 6/2005 | Michaelis et al. |
| 2007/0014776 | A1 | 1/2007 | Gimeno et al. |

FOREIGN PATENT DOCUMENTS

JP         11139984        5/1999

OTHER PUBLICATIONS

Bolon, 2004, Basic & Clinical Pharmacology & Toxicology, vol. 95, pp. 154-161.*

(Continued)

*Primary Examiner* — Robert Landsman
(74) *Attorney, Agent, or Firm* — Parker Highlander PLLC

(57) ABSTRACT

The present invention relates to agents, and methods for identifying compounds, which agents and compounds are effective in the treatment, and more particularly, that inhibit cachexia, and its associated or related disorders and conditions. In addition, the invention relates to compositions and methods for the use thereof in treating conditions that are characterized by cachexia, and its associated or related disorders and conditions and/or cachexia, and its associated or related disorders and conditions, such as for example, cancer cachexia and cachexia associated with AIDS, autoimmune disorders, drug addiction, alcoholism, chronic inflammatory disorders, cirrhosis of the liver, anorexia and neurodegenerative disease. In particular, the diagnostic marker and drug target of the invention is the ATGL Lipase, which can be inhibited by e.g. siRNAs and compounds with any of the following structures (I).

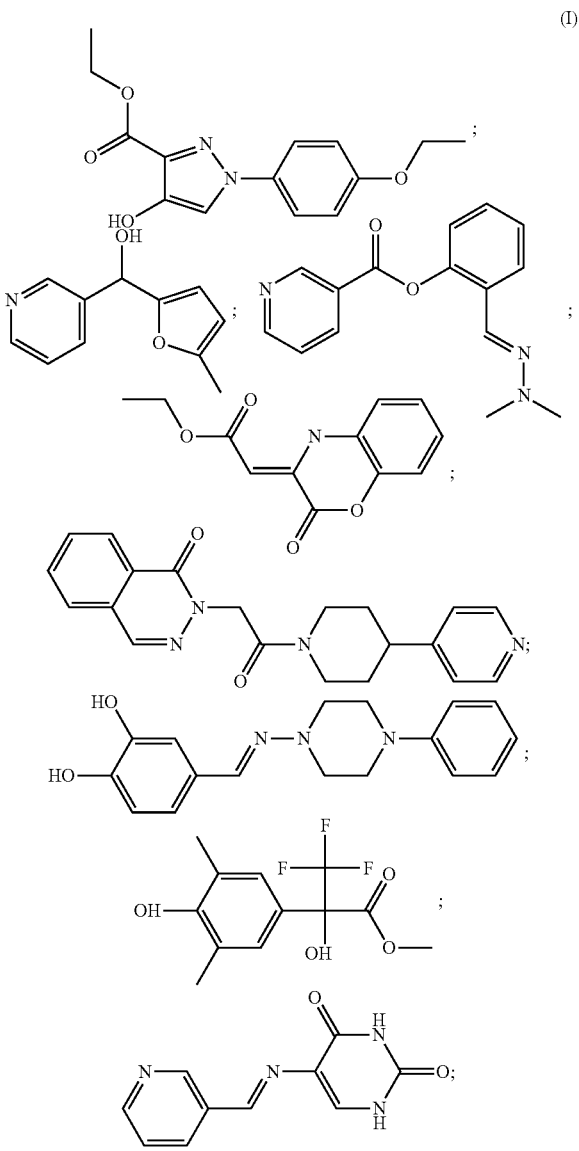

9 Claims, 9 Drawing Sheets

(51) Int. Cl.
| | |
|---|---|
| *A01N 57/00* | (2006.01) |
| *A61K 31/66* | (2006.01) |
| *A01N 43/00* | (2006.01) |
| *A61K 31/33* | (2006.01) |
| *A01N 43/58* | (2006.01) |
| *A61K 31/50* | (2006.01) |
| *A01N 43/40* | (2006.01) |
| *A61K 31/435* | (2006.01) |
| *A01N 43/44* | (2006.01) |
| *C12Q 1/44* | (2006.01) |
| *A61K 31/41* | (2006.01) |
| *A61K 31/495* | (2006.01) |

(52) U.S. Cl.
CPC ....... *G01N 2333/92* (2013.01); *G01N 2500/02* (2013.01); *G01N 2500/10* (2013.01); *G01N 2500/20* (2013.01); *G01N 2800/02* (2013.01); *G01N 2800/042* (2013.01)
USPC ................ 514/1; 435/6.1; 435/7.8; 514/130; 514/131; 514/183; 514/247; 514/277; 514/356

(56) References Cited

OTHER PUBLICATIONS

Pasquo, 2012, PLoS ONE, vol. 7, Issue 2, e32555.*
Kolchanov, 1988, Journal of Molecular Evolution, vol. 27, pp. 154-162.*
Das, 2011, Science, vol. 333, pp. 233-238.*
Kershaw EE, et al. Diabetes. 65:148-157, Jan. 2006—available online at—DOI: 10.2337/diabetes.55.01.06.db05-0982.*
Stam TC, et al. Eur. J. Clin. Invest. 30(4):336-343, Apr. 2000. Available online at—DOI: 10.1046/j.1365-2362.2000.00632.x.*
Kralisch S, et al. Mol. Cell. Endocrinol. 240:43-49, 2005—available online at—DOI: 10.1016/j.mce.2005.06.002.*
Kardos GG. N. Engl. J. Med. 274:868-873, Apr. 21, 1966—available online at—DOI: 10.1056/NEJM196604212741602.*

Agustsson et al. "Mechanism of increased lipolysis in cancer cachexia." Cancer Res. Jun. 1, 2007;67(11):5531-7.
Chung et al. "Anti-angiogenic pigment epithelium-derived factor regulates hepatocyte triglyceride content through adipose triglyceride lipase (ATGL)." J Hepatol. Mar. 2008;48(3):471-8. doi: 10.1016/j.jhep.2007.10.012. Epub Dec. 26, 2007.
Hoefler et al. "The role of lipases in the development of tumor-associated cachexia and tumormetabolism." Institute of Pathology, Medical University of Graz.
Jenkens et al. "Identification, Cloning, Expression, and Purification of Three Novel Human Calcium-independent Phospholipase A2 Family Members Possessing Triacylglycerol Lipase and Acylglycerol Transacylase Activities." Journal of Biological Chemistry. vol. 279, No. 47, Issue of Nov. 19, pp. 48968-48975, 2004.
McMillan et al. "A pilot study of megestrol acetate and ibuprofen in the treatment of cachexia in gastrointestinal cancer patients." Br J Cancer. 1997;76(6):788-90.
PCT International Search Report issued in International Application No. PCT/EP2010/054363, mailed Sep. 28, 2010.
WO 2005/014645. "PEDF-R Receptor and Uses." Becerra et al. Feb. 17, 2005.
WO 2005/115461, "Pharmaceutical Composition for Modulating the Activity of Triglyceride Hydrolase." Zechner et al. Dec. 8, 2005.
WO 2007/039232, "Means and Methods for Diagnosing ATGL Related Disorders." Kronenberg et al. Apr. 12, 2007.
WO 2008/013963, "Fatty Acid Amide Hydrolase Inhibitors." Makriyannis et al. Jan. 31, 2008.
WO 20090/11850, "Novel Therapeutic Compounds." Fix-Stenzel et al. Jan. 22, 2009.
Zimmermann et al. "Fat mobilization in adipose tissue is promoted by adipose triglyceride lipase." Science. Nov. 19, 2004;306(5700):1383-6.
Mayer et al., "Development of small-molecule inhibitors targeting adipose triglyceride lipase," *Nature Chemical Biology*, 9(12):785-787, 2013.
Schweiger et al., "The C-terminal region of human adipose triglyceride lipase affects enzyme activity and lipid droplet binding," *J. Biol. Chem.*, 283:17211-17220, 2008.

* cited by examiner

FIGURE 1
A
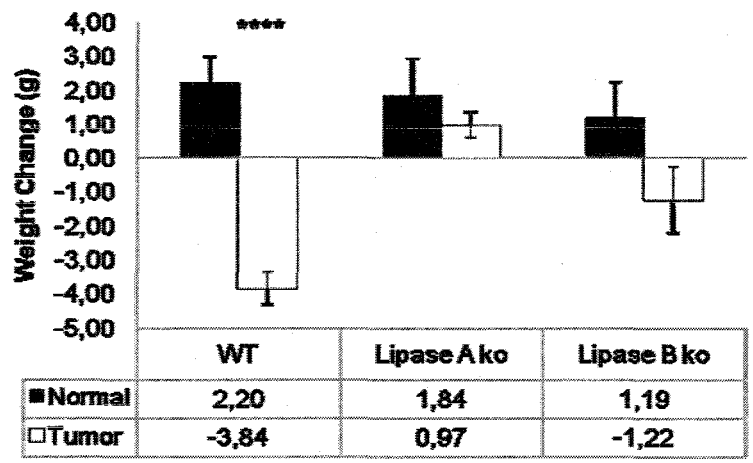
B
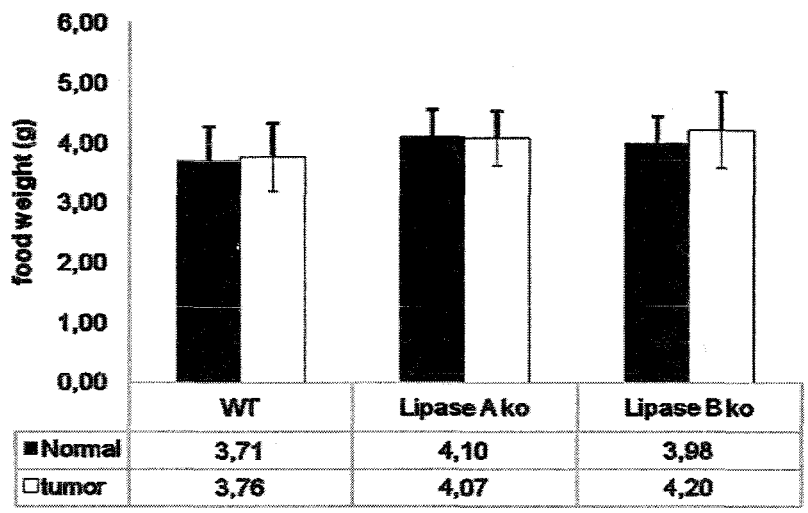

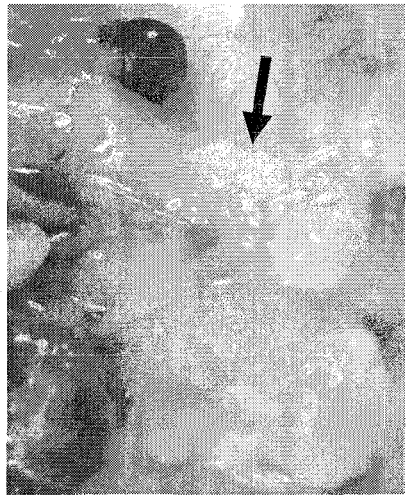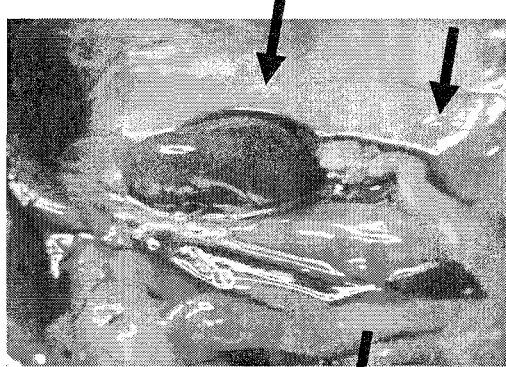
FIGURE 2

FIGURE 3
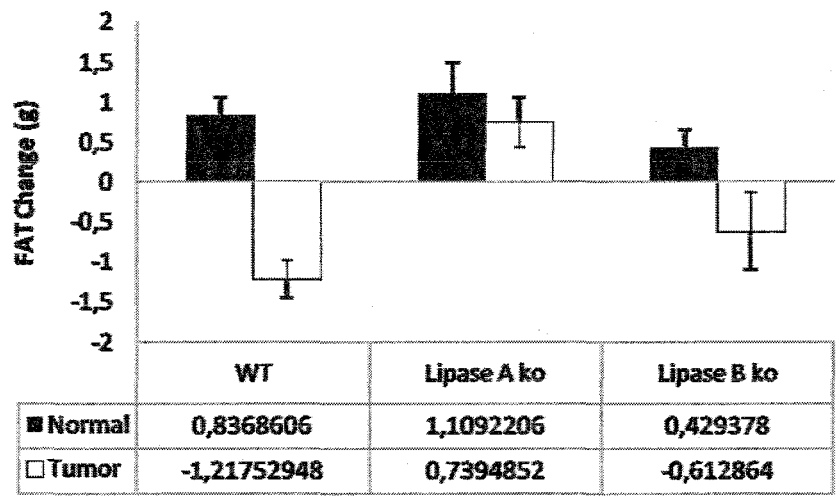
A
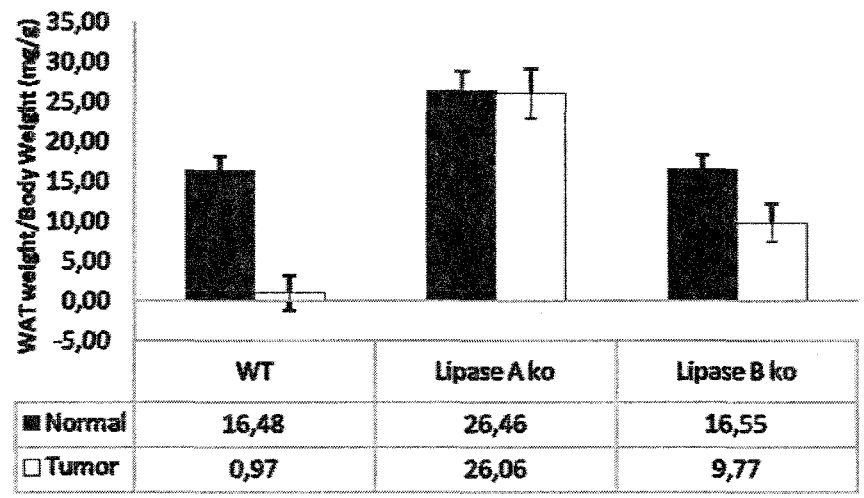
B

FIGURE 5
A
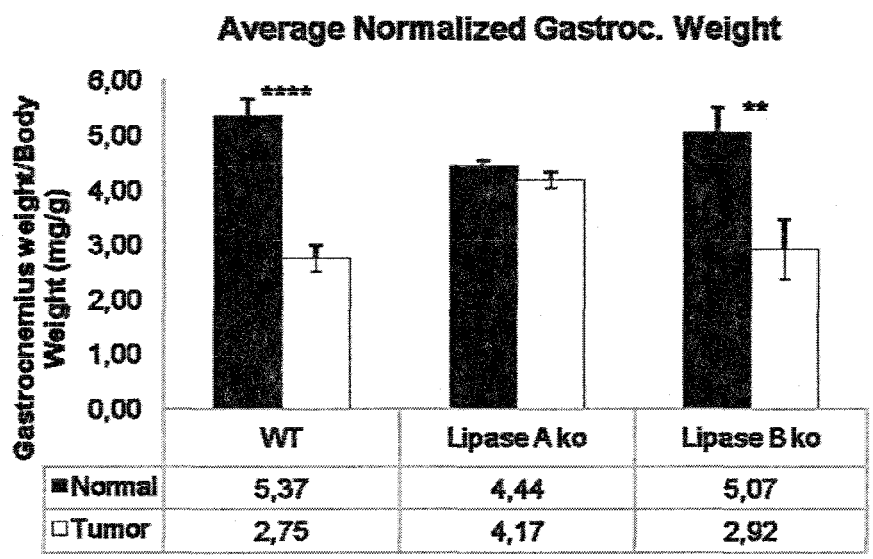
B
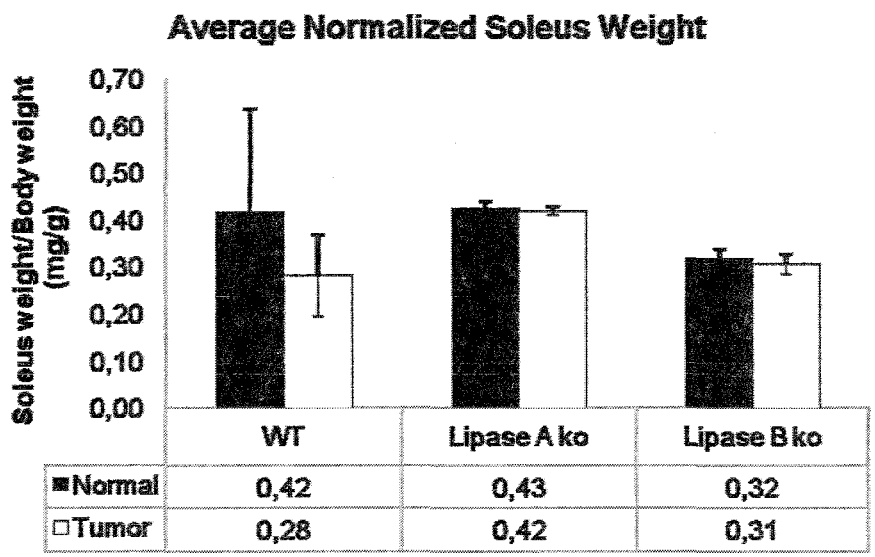

FIGURE 6
A
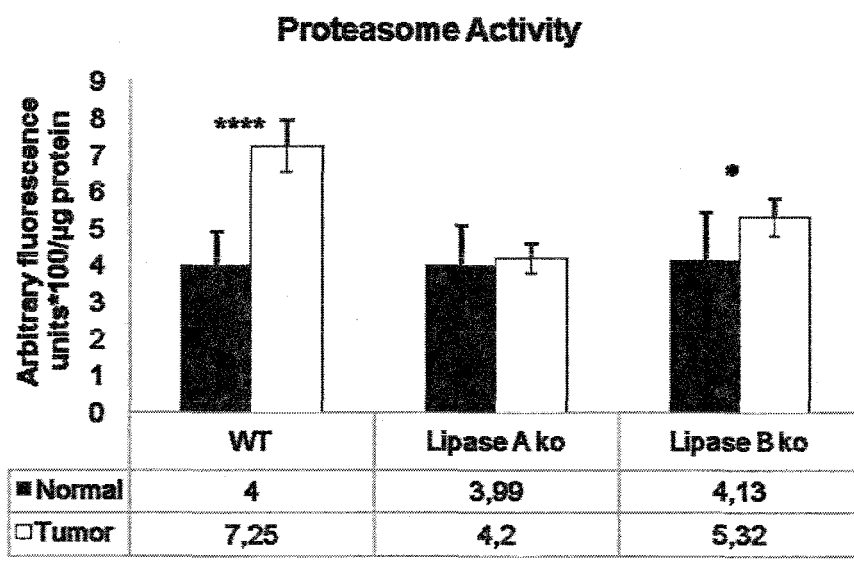
B
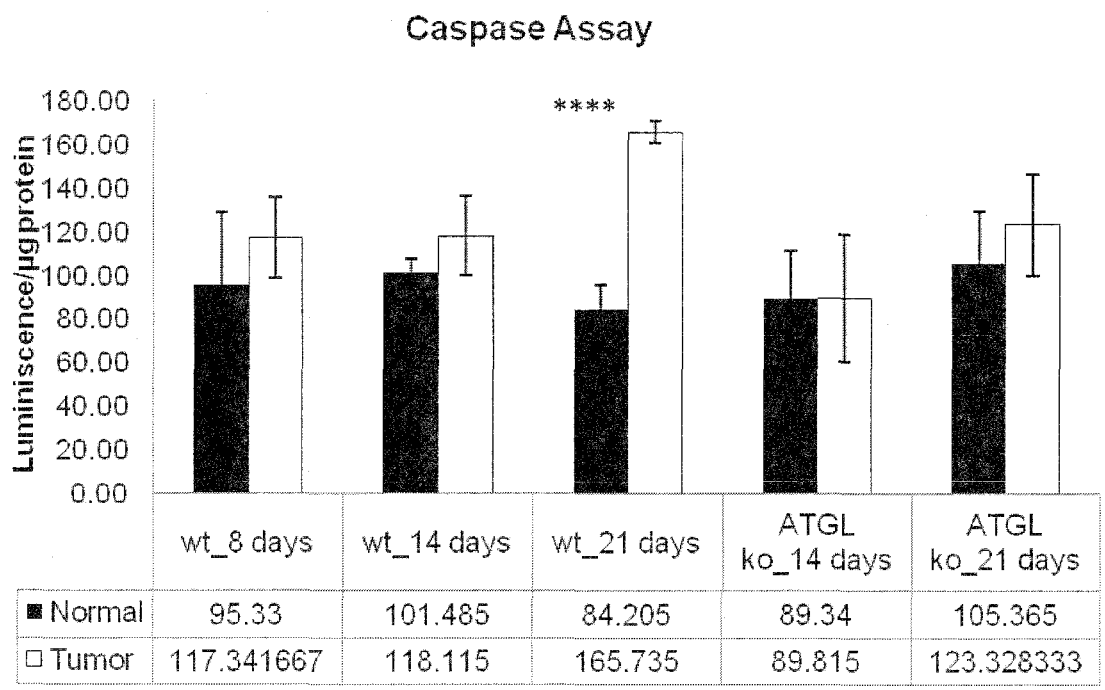

FIGURE 7

Human ATGL amino acid sequence

```
  1 mfprektwni sfagcgflgv yyvgvasclr ehapflvana thiygasaga ltatalvtgv
 61 clgeagakfi evskearkrf lgplhpsfnl vkiirsfllk vlpadsheha sgrlgisltr
121 vsdgenviis hfnskdeliq anvcsgfipv ycglippslq gvryvdggis dnlplyelkn
181 titvspfsge sdicpqdsst nihelrvtnt siqfnlrnly rlskalfppe plvlremckq
241 gyrdglrflq rngllnrpnp llalpparph gpedkdqave saqaedysql pgedhilehl
301 parlnealle acveptdllt tlsnmlpvrl atammvpytl plesalsfti rllewlpdvp
361 edirwmkeqt gsicqylvmr akrklgrhlp srlpeqvelr rvqslpsvpl scaayrealp
421 gwmrnnlslg dalakweecq rqllllglfct nvafppealr mrapadpapa padpaspqhq
481 lagpapllst papearpvig algl
```

Human ATGL nucleic acid

```
   1 gcggccccag tcagacgcag gcagccccaa agcctgaaca ggcagggcca gacccagctt
  61 cttcgcctcc gccagcgggg accccgagct agagccgcag cgggacctgc ccggcccccg
 121 gctccagcga gcgagcggcg agcaggcggc tcacagaggc ctggccgccc acggaacccg
 181 gggcccggcg gccgccgccg cgatgtttcc ccgcgagaag acgtggaaca tctcgttcgc
 241 gggctgcggc ttcctcggcg tctactacgt cggcgtggcc tcctgcctcc gcgagcacgc
 301 gcccttcctg gtggccaacg ccacgcacat ctacggcgcc tcggccgggg cgctcacggc
 361 cacggcgctg gtcaccgggg tctgcctggg tgaggctggt gccaagttca ttgaggtatc
 421 taaagaggcc cggaagcggt tcctgggccc cctgcacccc tccttcaacc tggtaaagat
 481 catccgcagt ttcctgctga aggtcctgcc tgctgatagc catgagcatg ccagtgggcg
 541 cctgggcatc tccctgaccc gcgtgtcaga cggcgagaat gtcattatat cccacttcaa
 601 ctccaaggac gagctcatcc aggccaatgt ctgcagcggt tcatccccg tgtactgtgg
 661 gctcatccct ccctccctcc aggggtgcg ctacgtggat ggtggcattt cagacaacct
 721 gccactctat gagcttaaga acaccatcac agtgtccccc ttctcgggcg agagtgacat
 781 ctgtccgcag gacagctcca ccaacatcca cgagctgcgg gtcaccaaca ccagcatcca
 841 gttcaacctg cgcaacctct accgcctctc caaggccctc ttccgccgg agcccctggt
 901 gctgcgagag atgtgcaagc agggataccg ggatggcctg cgctttctgc agcggaacgg
 961 cctcctgaac cggccaaacc ccttgctggc gttgccccc gcccgccccc acggcccaga
1021 ggacaaggac caggcagtgg agagcgccca agcggaggat tactcgcagc tgccgggaga
1081 agatcacatc ctggagcacc tgcccgcccg gctcaatgag gccctgctgg aggcctgcgt
1141 ggagcccacg gacctgctga ccaccctctc caacatgctg cctgtgcgtc tggccacggc
1201 catgatggtg ccctacacgc tgccgctgga gagcgctctg tccttcacca tccgcttgct
1261 ggagtggctg cccgacgttc ccgaggacat ccggtggatg aaggagcaga cgggcagcat
1321 ctgccagtac ctggtgatgc gcgccaagag gaagctgggc aggcacctgc cctccaggct
1381 gccggagcag gtggagctgc gccgcgtcca gtcgctgccg tccgtgccgc tgtcctgcgc
1441 cgcctacaga gaggcactgc ccggctggat gcgcaacaac ctctcgctgg gggacgcgct
1501 ggccaagtgg gaggagtgcc agcgccagct gctgctcggc ctcttctgca ccaacgtggc
1561 cttcccgccc gaagctctgc gcatgcgcgc acccgccgac ccggctcccg ccccgcgga
1621 cccagcatcc ccgcagcacc agctggccgg gcctgccccc ttgctgagca ccctgctcc
1681 cgaggcccgg cccgtgatcg gggccctggg gctgtgagac cccgaccctc tcgaggaacc
1741 ctgctgaga cgcctccatt accactgcgc agtgagatga ggggactcac agttgccaag
1801 aggggtcttt gccgtgggcc cctcgccag ccactcacca gctgcatgca ctgagagggg
1861 aggtttccac accctcccc tgggccgctg aggcccgcg cacctgtgcc ttaatcttcc
1921 ctcccctgtg ctgcccgagc cctcccccg ccccctttact cctgagaact ttgcagctgc
1981 ccttccctcc ccgttttca tggcctgctg aaatatgtgt gtgaagaatt atttatttc
2041 gccaaagcac atgtaataaa tgctgcagcc caaaaaaaaa aaaaaaaaaa aaaaaaaaaa
2101 aaaaaaaaaa aaa
```

FIGURE 8

Mouse ATGL amino acid sequence

```
  1 mftretkwni sfagcgflgv yhigvasclr ehapflvana thiygasaga ltatalvtga
 61 clgeaganii evskearkrf lgplhpsfnl vktirgcllk tlpadchera ngrlgisltr
121 vsdgenviis hfsskdeliq anvcstfipv ycglippttlq gvryvdggis dnlplyelkn
181 titvspfsge sdicpqdsst nihelrvtnt siqfnlrnly rlskalfppe pmvlremckq
241 gyrdglrflr rnalleacve pkdlmttlsn mlpvrlatam mvpytlples avsftirlle
301 wlpdvpedir wmkeqtgsic qylvmrakrk lgdhlpsrls eqvelrraqs lpsvplscat
361 ysealpnwvr nnlslgdala kweecqrqll lglfctnvaf ppdalrmrap asptaadpat
421 pqdppglppc
```

Mouse ATGL nucleic acid

```
   1 acagcgtctc cgcctccgcc ggcggagacc ccaaggtatc gagactgcgg gacccactgc
  61 ccgcaggaca tcgagtcacg atgttcacga gggagaccaa gtggaacatc tcattcgctg
 121 gctgcggctt cctcggggtc taccacattg gcgtggcctc ctgcctccgt gagcacgcgc
 181 ccttcctggt ggccaacgcc actcacatct acggagcctc ggcaggggcg ctcaccgcca
 241 cagcgctggt cactggggcc tgcctgggtg aagcaggtgc caacattatt gaggtgtcca
 301 aggaggcccg gaagcggttc ctgggtcctc tgcatccctc cttcaacctg gtgaagacca
 361 tccgtggctg tctactaaag accctgcctg ctgattgcca tgagcgcgcc aatggacgcc
 421 tgggcatctc cctgactcgt gtttcagacg gagagaacgt catcatatcc cactttagct
 481 ccaaggatga gctcatccag gccaatgtct gcagcacatt tatcccggtg tactgtggcc
 541 tcattcctcc tacccctcaa ggggtgcgct atgtggatgg cggcatttca gacaacttgc
 601 cactttatga gctgaagaat accatcacag tgtccccatt ctcaggcgag agtgacatct
 661 gccctcagga cagctccacc aacatccacg agcttcgcgt caccaacacc agcatccagt
 721 tcaaccttcg caatctctac cgcctctcga aggctctctt cccgccagag cccatggtcc
 781 tccgagagat gtgcaaacag gctacagag atggacttcg attccttagg aggaatgccc
 841 tgctggaggc ctgtgtggaa ccaaaggacc tgatgaccac cctttccaac atgctaccag
 901 tgcgcctggc aacggccatg atggtgccct atactctgcc gctggagagt gcagtgtcct
 961 tcaccatccg cttgttggag tggctgcctg atgtccctga agatatccgg tggatgaaag
1021 agcagacggg tagcatctgc cagtatctgg tgatgagggc caagaggaaa ttgggtgacc
1081 atctgccttc cagactgtct gagcaggtgg aactgcgacg tgcccagtct ctgccctctg
1141 tgccactgtc ttgcgccacc tacagtgagg ccctacccaa ctgggtacga acaacctct
1201 cactggggga cgcgctggcc aagtgggaag aatgccagcg tcagctactg ctgggtctct
1261 tctgcaccaa tgtggccttc ccgccggatg ccttgcgcat gcgcgcacct gccagcccca
1321 ctgccgcaga tcctgccacc ccacaggatc cacctggcct cccgccttgc tgagaatcac
1381 cattcccaca tcgcccggct accagccaag ctccaagttg tcctgcccca ctaagaggag
1441 ccccggggtg aacaagatc ctgtctgccc cggctctccc cttacatgc tgtggaatga
1501 ggacatagga ccctgcacag ctgcaagtgg gctttcgatg tgaaaccttt caccagccac
1561 tcactatgct actcctggtg gggagggatg gggagtcgcc ctccccgga gcccacagag
1621 ccctcccccg tcacgtcacc tgtgccttac tcctgcccac cacctttca gtgcagggtc
1681 agtcttaaga actccacatc tgctgctgct ccctggtgtc caagtttcct tgcagagtgt
1741 gtgaagaatt atttattttt gccaaagcag atctaataaa agccacagct cagcttctg
```

METHOD FOR TREATMENT OF CACHEXIA BY ADMINISTERING INHIBITORS OF ADIPOSE TRIGLYCERIDE LIPASE EXPRESSION OR ACTIVITY

The present application is a national phase application under 35 U.S.C. §371 of International Application No. PCT/EP2010/054363 filed Mar. 31, 2010 which claims priority to U.S. Provisional Application 61/211,604 filed Mar. 31, 2009 the entire text and figures of which disclosures are incorporated herein by reference without disclaimer.

The sequence listing that is contained in the file named "VOSSP0032US_ST25.txt", which is 15 KB (as measured in Microsoft Windows®) and was created on Nov. 27, 2013, is filed herewith by electronic submission and is incorporated by reference herein.

FIELD OF THE INVENTION

The present invention relates to methods of prevention, treatment or alleviation of cachexia and other wasting syndromes or conditions of loss of weight and/or muscle atrophy by modulation, including inhibition, of lipase, particularly adipose triglyceride lipase (ATGL). The invention relates to agents, and methods for identifying compounds, which agents and compounds result in the inhibition of lipase, particularly ATGL, and the alleviation of cachexia or related conditions or disorders.

BACKGROUND OF THE INVENTION

Animals, seed plants, and fungi commonly store excessive amounts of energy substrates in the form of intracellular triglyceride (TG) deposits. In mammals, TG are stored in adipose tissue providing the primary source of energy during periods of food deprivation. Whole body energy homeostasis depends on the precisely regulated balance of lipid storage and mobilization. Mobilization of fatty acids from triglyceride stores in adipose tissue critically depends on the activation of lipolytic enzymes, which degrade adipose TG and release non-esterified fatty acids (FA) into the circulation. Dysfunctional lipolysis affects energy homeostasis and may contribute to the pathogenesis of obesity and insulin resistance. Dysregulation of TG-lipolysis in man has been linked to variation in the concentration of circulating FA, an established risk factor for the development of insulin resistance (Bergman, R. N. et al (2001) J Investig Med 49: 119-26; Blaak, E. E. (2003) Proc Nutr Soc 62: 753-60; Boden, G. and G. I. Shulman (2002) Eur J Clin Invest 32(Suppl 3):14-23; Arner, P. (2002) Diabetes Metab Res Rev 18(Suppl 2): S5-9).

During periods of increased energy demand, lipolysis in adipocytes is activated by hormones, such as catecholamines. Hormone interaction with G-protein coupled receptors is followed by increased adenylate cyclase activity, increased cAMP levels, and the activation of cAMP-dependent protein kinase (protein kinase A, PKA) (Collins, S. and R. S. Surwit (2001) Recent Prog Horm Res 56:309-28). PKA then phosphorylates targets with established function in lipolysis including hormone-sensitive lipase (HSL), resulting in the translocation of HSL from the cytoplasm to the lipid droplet where efficient TG hydrolysis occurs (Sztalryd, C. et al (2003) J Cell Biol 161:1093-103).

The mobilization of free fatty acids from adipose triacylglycerol (TG) stores requires the activities of triacylglycerol liposis. Adipose triglyceride lipase (ATGL) and hormone-sensitive lipase (HSL) are the major enzymes contributing to TG breakdown. ATGL (also named PNPLA 2 (patatin-like phospholipase domain containing protein-2, desnutrin, phospholipase A2δ, and transport-secretion protein)) is highly expressed in adipose tissue and specifically removes the first fatty acid from the TG molecule, generating FFA and DG (Zimmerman, R. et al (2006) Science 306:1383-1386; Wang, S P et al (2001) Obes Res 9:119-128; Villena, J A et al (2004) J Biol Chem 279:47066-47075; Jenkins, C M et al (2004) J Biol Chem 279:48968-48975). An essential role of ATGL in lipolypsis has been demonstrated in studies of ATGL-deficient (ATGL-ko) mice (Haemmerle, G. et al (2006) Science 312:734-737). ATGL-deficient mice accumulated large amounts of lipid in the heart, causing cardiac dysfunction and premature death. The relative contribution of these hydrolases to the lipolytic catabolism of fat has been determined, including in mutant mouse models lacking ATGL or HSL (Schweiger, M. et al (2006) J Biol Chem 281(52):40236-40241). Both HSL and ATGL enzymes contribute to hydrolysis of TG, however, ATGL deficient mice studies indicate that ATGL is rate limiting in the catabolism of cellular fat deposits and plays an important role in energy homeostasis (Haemmerle, G. et al (2006) Science 312(5774):734-737).

Cachexia is loss of weight, muscle atrophy, fatigue, weakness and significant loss of appetite in someone who is not actively trying to lose weight. It can be a sign of various underlying disorders; when a patient presents with cachexia, a doctor will generally consider the possibility of cancer, certain infectious diseases (e.g. tuberculosis, AIDS), and some autoimmune disorders, or addiction to drugs such as amphetamines or cocaine, chronic alcoholism and cirrhosis of the liver. Cachexia physically weakens patients to a state of immobility stemming from loss of appetite, asthenia, and anemia, and response to standard treatment is usually poor (Lainscak M, et al (2007) Curr Opin Support Palliat Care 1(4): 299-305; Bossola M et al (2007) Expert Opin Investig Drugs 16 (8): 1241-53).

Cachexia is often seen in end-stage cancer, and in that context is called "cancer cachexia". It was also prevalent in HIV patients before the advent of highly active anti-retroviral therapy (HAART) for that condition; now it is seen less frequently in those countries where such treatment is available. In those patients who have Congestive Heart Failure, there is also a cachectic syndrome. Also, a cachexia co-morbidity is seen in patients that have any of the range of illnesses classified as "COPD" (chronic obstructive pulmonary disease), particularly emphysema. Some severe cases of schizophrenia can present this condition where it is named vesanic cachexia (from vesania, a Latin term for insanity).

The exact mechanism by which these diseases cause cachexia is poorly understood, but there is postulated a role for inflammatory cytokines such as tumor necrosis factor-alpha (TNF-α), interleukins 1 and 6 (IL-1 and IL-6), interferon gamma (IFN-γ), leukemia-inhibitory factor (LAF), as well as ZAG, a 43 kDa soluble glycoprotein as mediators of the cachectic process. However, the results of a number of clinical and laboratory studies suggest that the action of the cytokines alone is unable to explain the complex mechanism of wasting in cancer cachexia. In addition, cachexia has been observed in some xenograft models even with concomitant administration of anti-TNF-α antibody without a cytokine involvement, suggesting that TNF-α may not be responsible for the cachexia and that other factors may be involved (Costelli P et al (1993) J Clin Invest 92:2783-2789; Sherry B A et al (1989) FASEB J 3:1956-1962).

About half of all cancer patients show a syndrome of cachexia, characterized by loss of adipose tissue and skeletal muscle mass. Such patients have a decreased survival time, compared with the survival time among patients without weight loss, and loss of total body protein leads to substantial impairment of respiratory muscle function. The definitive treatment of cancer cachexia is removal of the causative tumor. Short of achieving this goal, which is often compromised by the patients' inability to tolerate cancer treatments due to their cachexia, various measures have been undertaken to ameliorate cachexia, however with limited success. Various agents have been administered in attempts to retard or halt progressive cachexia in cancer patients. These agents include orexigenic agents (appetite stimulants), corticosteroids, cannabinoids, serotonin antagonists, prokinetic agents, androgens and anabolic agents, anticytokine agents, NSAIDs, and regulators of circadian rhythm.

Despite an increased understanding of ATGL and its role in TG hydrolysis and lipolysis, there is still a need for a fuller and specific understanding of its physiological role and its potential application and/or role in pathological conditions. Cachexia and other relevant wasting syndromes provide a significant and largely unaddressed condition. Improved and specific therapies for these conditions and for the particular modulation of the fat and muscle wasting associated therewith are needed.

The citation of references herein shall not be construed as an admission that such is prior art to the present invention.

SUMMARY OF THE INVENTION

In its broadest aspect, the present invention extends to the recognition that inhibition of lipase activity provides a novel approach to prevention, treatment and/or alleviation of cachexia, and its associated or related disorders and conditions, including weight loss, muscle atrophy or wasting, and reduction of white adipose tissue (WAT). Thus inhibition or reduction of the activity of lipases, particularly inhibition of ATGL alone or in combination with inhibition of HSL, is provided for the prevention, treatment and/or alleviation of cachexia, and its associated or related disorders and conditions, including weight loss, muscle atrophy or wasting, and reduction of WAT.

The present invention is based on the discovery that inhibition of the lipase ATGL by knockout or elimination of its expression in animal models results in prevention of cachexia in a lung cancer tumor-induced cachexia model system. ATGL inhibition maintains white adipose tissue, and muscle mass significantly in tumor-bearing animals versus either wild type or HSL inhibited animals. The present invention therefore provides ATGL as a TARGET which is involved in the pathway involved in cachexia, and its associated or related disorders and conditions, including weight loss, muscle atrophy or wasting. The invention includes methods of screening for agents capable of prevention, treatment or alleviation of cachexia, and its associated or related disorders and conditions, including weight loss, muscle atrophy or wasting, and uses of these agents in the prevention and/or treatment of cachexia, and its associated or related disorders and conditions, including weight loss, muscle atrophy or wasting.

The present invention relates to a method for identifying compounds that inhibit ATGL expression and/or activity, comprising contacting the compound with the identified TARGET (e.g., ATGL and/or HSL, alternative species forms, isoforms, and variants as further described herein below), or cells expressing the TARGET, or animals expressing the TARGET under conditions that allow said TARGET or active fragments or lipase domains thereof to bind to the compound, and measuring a property related to ATGL expression or activity, including but not limited to lipase activity, TG hydrolysis, fatty acid release, ATGL mRNA expression, ATGL protein levels, or physiological markers such as cachexia, body weight, WAT, and muscle mass.

Aspects of the present method include the in vitro assay of compounds using identified TARGET (e.g., ATGL and/or HSL, alternative species forms, isoforms, and variants as further described herein below), and cellular assays wherein identified TARGET inhibition is followed by observing indicators of efficacy, including alteration of the release of free fatty acid, TG hydrolysis, etc. Another aspect of the invention is a method of treatment or prevention of a condition involving cachexia, and its associated or related disorders and conditions, including weight loss, muscle atrophy or wasting, in a subject suffering or susceptible thereto, by administering a pharmaceutical composition comprising an agent which is able to inhibit ATGL. Also contemplated herein, are compositions comprising one or more ATGL-inhibiting agents of the invention, alone, or in combination with each other or in combinations with one or more inhibitors of inflammatory cytokines such as tumor necrosis factor-alpha (TNF-α), interleukins 1 and 6 (IL-1 and IL-6), interferon gamma (IFN-γ), and leukemia-inhibitory factor (LAF).

The present invention relates to a method for identifying compounds that inhibit the TARGET(s) (e.g., ATGL and/or HSL, alternative species forms, isoforms, and variants as further described herein below), comprising contacting the compound with the identified TARGET or active fragments or lipase domains thereof under conditions wherein the compounds may interact with or influence the TARGET(s), measuring the expression of ATGL, levels of TG, release of fatty acid, lipase activity, etc. and selecting compounds which alter, particularly inhibit or reduce the expression of ATGL, release of fatty acid, lipase activity, etc. or stabilize the levels of TG in the presence of other TG lipases such as HSL. In one such method the release of free fatty acid from adipose tissue is measured.

Aspects of the present method include the in vitro assay of compounds using polypeptide of a TARGET (e.g., ATGL and/or HSL, alternative species forms, isoforms, and variants as further described herein below), or fragments thereof, including the amino acid sequences described in FIG. 7 (human ATGL; SEQ ID NO: 1 shows the amino acid sequence and SEQ ID NO: 2 shows the cDNA including the coding sequence) and 8 (mouse ATGL; SEQ ID NO: 3 shows the amino acid sequence and SEQ ID NO: 4 shows the cDNA including the coding sequence) hereof and the publicly known sequences of ATGL, and cellular assays wherein TARGET inhibition is followed by observing indicators of efficacy including, for example, TARGET expression levels, TARGET enzymatic activity, release of FA, TG hydrolysis, lipase activity, and/or other assessments of fat, white adipose tissue, muscle mass, weight loss, and/or cachexia.

The present invention also relates to
(1) expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a TARGET (e.g., ATGL and/or HSL, alternative species forms, isoforms, and variants as further described herein below) polypeptide and
(2) pharmaceutical compositions comprising said agent(s), useful in the treatment, or prevention, of cachexia, and its associated or related disorders and conditions, including weight loss, muscle atrophy or wasting.

Another aspect of the invention is a method of treatment or prevention of a disease or condition characterized by fat loss, weight loss, muscle atrophy, wasting, anorexia, or cachexia, and in particular those diseases/conditions characterized by involuntary or unintended loss of weight, fat and/or muscle, in a subject suffering from or susceptible thereto, by administering a pharmaceutical composition comprising an effective TARGET (e.g., ATGL and/or HSL, alternative species forms, isoforms, and variants as further described herein below)-expression inhibiting amount of a expression-inhibitory agent or an effective TARGET activity inhibiting amount of an activity-inhibitory agent.

Another aspect of this invention relates to the use of agents which inhibit a TARGET as disclosed herein in a therapeutic method, a pharmaceutical composition, and the manufacture of such composition, useful for the treatment of a disease or condition involving cachexia, and its associated or related disorders and conditions. In particular, the present method relates to the use of the agents which inhibit a TARGET (e.g., ATGL and/or HSL, alternative species forms, isoforms, and variants as further described herein below) in the treatment of cachexia, and its associated or related disorders and conditions, including weight loss, muscle atrophy or wasting, fat loss, and/or reduced WAT.

Another aspect of this invention relates to the use of agents which inhibit a TARGET as disclosed herein in a therapeutic method, a pharmaceutical composition, and the manufacture of such composition, useful for the treatment of a disease involving cachexia, and its associated or related disorders and conditions, including weight loss, muscle atrophy or wasting, fat loss, and for reduced WAT.

Another aspect of this invention relates to the compounds of formula (I), (II), (III) or (IV) as described and defined herein below or the compounds described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)) for use as a medicament, in particular for use in the treatment or prevention of cachexia, or its associated or related disorders and conditions, including e.g. weight loss, muscle atrophy or wasting, fat loss, and/or reduced WAT.

A further aspect of the invention relates to a compound of formula (I), (II), (III) or (IV) as described and defined herein below or the compounds described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)). Preferably, the compound inhibits expression or activity of the TARGET. More preferably, the compound inhibits ATGL and/or HSL, alternative species forms, isoforms, and variants as further described herein below. Further preferably, the compound inhibits ATGL, alternative species forms, isoforms, and variants as further described herein below. More preferably, the compound specifically inhibits ATGL but does not inhibit other lipases, preferably HSL. In a preferred embodiment of the invention, the compound inhibits ATGL activity when present in micromolar, more preferably in nanomolar concentration. In a preferred embodiment, the compound inhibits human ATGL, the amino acid sequence of which is shown in FIG. 7 and SEQ ID NO: 1. Measuring lipase activity and the activity of a lipase inhibitor can be accomplished by methods known to those skilled in the art. Preferably, the inhibition of lipase activity, wherein lipase is preferably ATGL, is measured as described herein below in Example 3, using measurements of lipolytic activity as described in Examples 1 and 2 herein below. In a preferred embodiment of the invention, the method as described herein in paragraph [0243] to [0247] in Example 2 herein, including references made therein, is used. A preferred embodiment of the invention includes measurement of lipase activity according to Jenkins et al. and Chung et al., as described in Example 2 herein. A further preferred embodiment of the invention includes measurement of lipase activity as described in paragraph [0246] in Example 2 herein and references made therein. A further preferred embodiment of the invention includes measurement of lipase activity as described in paragraph [2047] in Example 2 herein and references made therein. Any such assays and tests are described for the purpose of illustration and guidance; variations, alterations, adaptations and modifications will be obvious and possible to the person of skill in the art. For instance, the test described in paragraphs [0246] or [0247] may be used to test the lipolytic activity and if desired the inhibition thereof by a given inhibitor, among others, of variants, fragments, variants due to premature termination or the like, of a lipase, preferably of ATGL lipase, without deviating from the scope of the invention.

Other objects and advantages will become apparent from a consideration of the ensuing description taken in conjunction with the following illustrative drawings.

BRIEF DESCRIPTION OF THE FIGURES

FIGS. 1A and 1B. A: depicts average weight change for WT, Lipase A (ATGL) ko mice and Lipase B (HSL) ko mice. Weight changes compared to the initial weight is depicted in g for tumor bearing animals and normal mock injected animals; tumor tissue weight was subtracted from the body weight. B: depicts average food weight per day for WT, Lipase A (ATGL) ko mice and Lipase B (HSL) ko mice. Food intake was recorded daily. Average daily food consumption is given in g.

FIGS. 2A, 2B and 2C depict visual inspections of white adipose tissue (WAT) in tumor bearing mice. A shows no visible fat in tumor bearing wildtype mice. B shows that WAT is preserved in tumor bearing ATGL ko mice. WAT is clearly evident at the arrow indicated. C depicts a closer view of preserved perirenal WAT in ATGL ko mice at arrows where indicated.

FIGS. 3A and 3B. A: WAT weight normalized to body weight (mg/g) is given for mock injected and tumor bearing wildtype, Lipase A (ATGL) ko mice and Lipase B (HSL) ko mice. Almost identical results were obtained when WAT was normalized to the length of the tibia bone. B: Average fat change by NMR for mock injected and tumor bearing wildtype, Lipase A (ATGL) ko mice and Lipase B (HSL) ko mice. NMR analysis for the assessment of total body fat content was performed before injection and immediately before sacrificing the animals respectively. Using NMR analysis, fat content is recorded as percentage and total fat weight is calculated from the animals' weight. Change (in g) is reported compared to the initial values before injection.

FIGS. 5A and 5B. A: depicts average normalized gastrocnemius muscle weight and B: depicts average normalizes soleus muscle weight in mock injected and tumor bearing mice including wildtype, Lipase A (ATGL) ko mice, and Lipase B (HSL) ko mice. 21 days after injection of tumor cells or mock injections, mice were sacrificed. *M. gastrocnenius* and *M. soleus* were dissected from both hind legs and the weight recorded. Muscle weight normalized to body weight is compared to the mock injected animals.

FIGS. 6A and 6B. A depicts proteasome activity in mock injected and tumor bearing mice including wildtype, Lipase A (ATGL) ko mice, and Lipase B (HSL) ko mice. B depicts caspase activity in mock injected and tumor bearing mice including wildtype and Lipase A (ATGL) ko mice. Wildtype mice were measured at 8, 14 and 21 days, and Lipase A mice were measured at 14 and 21 days. Proteasome as well as caspase activities were measured in muscle homogenates. Values (arbitrary fluorescence or luminescence respectively) were normalized to protein concentration and compared to mock injected animals.

FIG. 7 as well as SEQ ID NOs: 1 and 2 depict the amino acid and cDNA including the nucleic acid coding sequence, respectively, of human ATGL. These sequences correspond to Genbank NM_020376 (nucleotide) and NP_065109 (protein).

FIG. 8 as well as SEQ ID NOs: 3 and 4 depict the amino acid and cDNA including the nucleic acid coding sequence, respectively, of mouse ATGL. These sequences correspond to Genbank NM_025802 (nucleotide) and NP_080078 (protein).

DETAILED DESCRIPTION OF THE INVENTION

Figure 4:
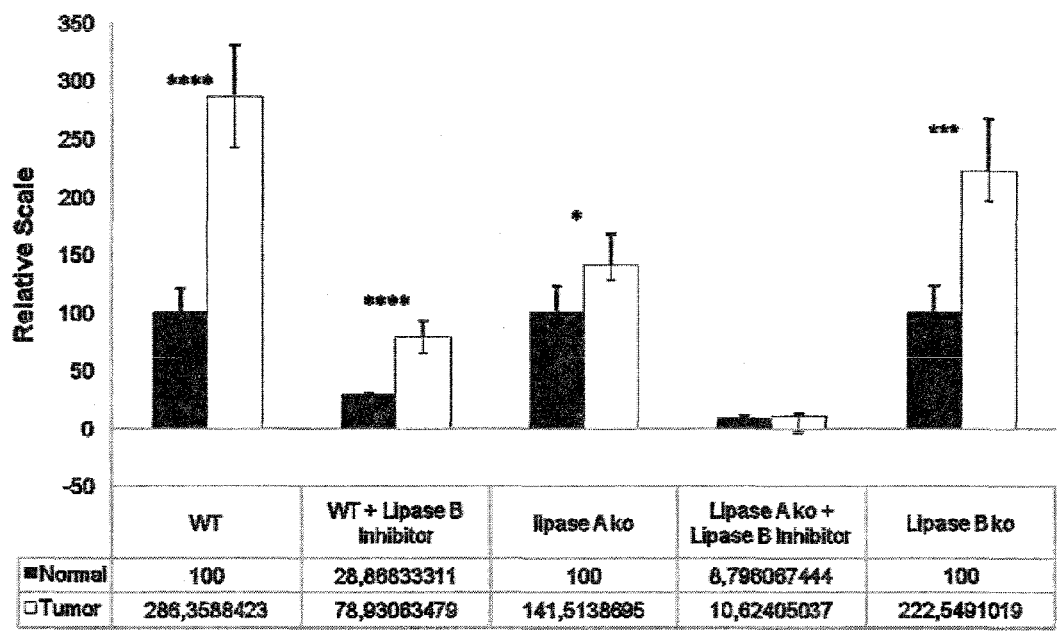
FIG. 4 depicts results of lipase assay of mock injected and tumor bearing mice including wildtype, Lipase A (ATGL) ko mice, and Lipase B (HSL) ko mice, in the presence or absence of a lipase B inhibitor. Animals were sacrificed 14 days after injection of tumor cells or mock injection, a time point where adipose tissue still can be dissected from wild type tumor bearing mice. Lipase activity was measured in homogenates of adipose tissue without (total lipase activity) or with inhibition of HSL (Lipase B) using an HSL inhibitor.

The following terms are intended to have the meanings presented therewith below and are useful in understanding the description and intended scope of the present invention.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

As used herein, the term 'antagonist' is used to describe a compound that does not provoke a biological response itself upon binding to a receptor, but blocks or dampens agonist-mediated responses, or prevents or reduces agonist binding and, thereby, agonist-mediated responses.

The term 'assay' means any process used to measure a specific property of an agent. A 'screening assay' means a process used to characterize or select agents based upon their activity from a collection of agents.

The term 'binding affinity' is a property that describes how strongly two or more compounds associate with each other in a non-covalent relationship. Binding affinities can be characterized qualitatively (such as 'strong', 'weak', 'high', or 'low') or quantitatively (such as measuring the $K_D$).

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term 'complex' means the entity created when two or more compounds bind to, contact, or associate with each other.

The term 'compound' is used herein in the context of a 'test compound' or a 'drug candidate compound' described in connection with the assays of the present invention. As such, these compounds comprise organic or inorganic compounds, derived synthetically, recombinantly, or from natural sources. The compounds include inorganic or organic compounds such as polynucleotides, lipids or hormone analogs. Other biopolymeric organic test compounds include peptides comprising from about 2 to about 40 amino acids and larger polypeptides comprising from about 40 to about 500 amino acids, including polypeptide ligands, enzymes, receptors, channels, antibodies or antibody conjugates.

The term 'condition' or 'disease' means the overt presentation of symptoms (i.e., illness) or the manifestation of abnormal clinical indicators (for example, biochemical indicators or diagnostic indicators). Alternatively, the term 'disease' refers to a genetic or environmental risk of or propensity for developing such symptoms or abnormal clinical indicators.

The term 'contact' or 'contacting' means bringing at least two moieties together, whether in an in vitro system or an in vivo system.

The term 'derivatives of a polypeptide' relates to those peptides, oligopeptides, polypeptides, proteins and enzymes that comprise a stretch of contiguous amino acid residues of the polypeptide and that retain a biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents, or heterologous amino acid substituents, compared to the amino acid sequence of a naturally occurring form of the polypeptide, for example a reporter molecule or other ligand, covalently or non-covalently bound to the amino acid sequence.

The term 'derivatives of a polynucleotide' relates to DNA-molecules, RNA-molecules, and oligonucleotides that comprise a stretch of nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy)ethyl-phosphorothioate, non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term 'endogenous' shall mean a material that a mammal naturally produces. Endogenous in reference to the term 'protease', 'kinase', 'factor', or 'receptor' shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both in vivo and in vitro systems. For example, and without limitation, in a screening approach, the endogenous or non-endogenous TARGET (e.g., ATGL and/or HSL, alternative species forms, isoforms, and variants as further described herein below) may be in reference to an in vitro screening system. As a further example and not limitation, where the genome of a mammal has been manipulated to include a non-endogenous TARGET, screening of a candidate compound by means of an in vivo system is viable.

The term 'expressible nucleic acid' means a nucleic acid coding for a proteinaceous molecule, an RNA molecule, or a DNA molecule.

The term 'expression' comprises both endogenous expression and overexpression by transduction.

The term 'expression inhibitory agent' means a polynucleotide designed to interfere selectively with the transcription, translation and/or expression of a specific polypeptide or protein normally expressed within a cell. More particularly, 'expression inhibitory agent' comprises a DNA or RNA molecule that contains a nucleotide sequence identical to or complementary to at least about 15-30, particularly at least 17, sequential nucleotides within the polyribonucleotide sequence coding for a specific polypeptide or protein. Exemplary expression inhibitory molecules include ribozymes, double stranded siRNA molecules, self-complementary single-stranded siRNA molecules (shRNA), genetic antisense constructs, and synthetic RNA antisense molecules with modified stabilized backbones.

The term 'fragment of a polynucleotide' relates to oligonucleotides that comprise a stretch of contiguous nucleic acid residues that exhibit substantially a similar, but not necessarily identical, activity as the complete sequence. In a particular aspect, 'fragment' may refer to a oligonucleotide comprising a nucleic acid sequence of at least 5 nucleic acid residues (preferably, at least 10 nucleic acid residues, at least 15 nucleic acid residues, at least 20 nucleic acid residues, at least 25 nucleic acid residues, at least 40 nucleic acid residues, at least 50 nucleic acid residues, at least 60 nucleic acid residues, at least 70 nucleic acid residues, at least 80 nucleic acid residues, at least 90 nucleic acid residues, at least 100 nucleic acid residues, at least 125 nucleic acid residues, at least 150 nucleic acid residues, at least 175 nucleic acid residues, at least 200 nucleic acid residues, or at least 250 nucleic acid residues) of the nucleic acid sequence of said complete sequence.

The term 'fragment of a polypeptide' relates to peptides, oligopeptides, polypeptides, proteins, monomers, subunits and enzymes that comprise a stretch of contiguous amino acid residues, and exhibit substantially a similar, but not necessarily identical, functional or expression activity as the complete sequence. In a particular aspect, 'fragment' may refer to a peptide or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of said complete sequence.

The term 'hybridization' means any process by which a strand of nucleic acid binds with a complementary strand through base pairing. The term 'hybridization complex' refers to a complex formed between two nucleic acid sequences by virtue of the formation of hydrogen bonds between complementary bases. A hybridization complex may be formed in solution (for example, $C_{0t}$ or $R_{0t}$ analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency. The term 'standard hybridization conditions' refers to salt and temperature conditions substantially equivalent to 5×SSC and 65° C. for both hybridization and wash. However, one skilled in the art will appreciate that such 'standard hybridization conditions' are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined T, with washes of higher stringency, if desired.

The term 'inhibit' or 'inhibiting', in relationship to the term 'response' means that a response is decreased or prevented in the presence of a compound as opposed to in the absence of the compound.

The term 'inhibition' refers to the reduction, down regulation of a process or the elimination of a stimulus for a process, which results in the absence or minimization of the expression or activity of a protein or polypeptide.

The term 'induction' refers to the inducing, up-regulation, or stimulation of a process, which results in the expression or activity of a protein or polypeptide.

The term 'ligand' means a molecule, including an endogenous, naturally occurring or synthetic, non-natural molecules, specific for an endogenous, naturally occurring receptor.

The term 'pharmaceutically acceptable salts' refers to the non-toxic, inorganic and organic acid addition salts, and base addition salts, of compounds which inhibit the expression or activity of TARGETS as disclosed herein. These salts can be prepared in situ during the final isolation and purification of compounds useful in the present invention.

The term 'polypeptide' relates to proteins (such as TARGETS (e.g., ATGL and/or HSL, alternative species forms, isoforms, and variants as further described herein below)), proteinaceous molecules, fragments of proteins, monomers, subunits or portions of polymeric proteins, peptides, oligopeptides and enzymes (such as kinases, proteases, GPCR's etc.).

The term 'polynucleotide' means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more particularly 70 percent of its base pairs are in common, most particularly 90 percent, and in a particular embodiment, 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, particularly about 100 to about 4000 bases, more particularly about 250 to about 2500 bases. One polynucleotide embodiment comprises from about 10 to about 30 bases in length. A particular embodiment of polynucleotide is the polyribonucleotide of from about 17 to about 22 nucleotides, more commonly described as small interfering RNAs (siRNAs—double stranded siRNA molecules or self-complementary single-stranded siRNA molecules (shRNA)). Another particular embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection. Polynucleotides herein are selected to be 'substantially' complementary to different strands of a particular target DNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'solvate' means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term 'subject' includes humans and other mammals. In the context of this invention, it is particularly envisaged that mammals are to be treated which are economically, agronomically or scientifically important. Scientifically important organisms include, but are not limited to, mice, rats, and rabbits. Non-limiting examples of agronomically important animals are sheep, cattle and pigs, while, for example, cats and dogs may be considered as economically important animals. Preferably, the subject is a human.

'Therapeutically effective amount' means that amount of a drug, compound, expression inhibitory agent, or pharmaceutical agent that will elicit the biological or medical response of a subject that is being sought by a medical doctor or other clinician.

The term 'treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

The term "vectors" also relates to plasmids as well as to viral vectors, such as recombinant viruses, or the nucleic acid encoding the recombinant virus.

The term "vertebrate cells" means cells derived from animals having vertera structure, including fish, avian, reptilian, amphibian, marsupial, and mammalian species. Preferred cells are derived from mammalian species, and most preferred cells are human cells. Mammalian cells include feline, canine, bovine, equine, caprine, ovine, porcine murine, such as mice and rats, and rabbits.

The term 'TARGET' or 'TARGETS' means the protein(s) identified in accordance with the assays and methods described herein and determined to be involved in the modulation and/or prevention, treatment or alleviation of cachexia and its associated or related disorders and conditions, including weight loss, muscle atrophy or wasting, reduction of WAT, and reduction of fat. The term TARGET or TARGETS includes and contemplates lipases responsible for or contributing to the hydrolysis of triacylglycerides and lipolysis, particularly adipose triacylglycerol (TG), including ATGL and/or HSL, alternative species forms, isoforms, fragments and variants, such as splice variants, allelic variants, alternate in frame exons, and alternative or premature termination or start sites, including known or recognized isoforms or variants. Preferably, alternative species forms of ATGL, isoforms of ATGL, fragments of ATGL and variants of ATGL, such as splice variants, allelic variants, alternate in frame exons, and alternative or premature termination or start sites, are enzymatically or lipolytically active, e.g., are capable of removing the first fatty acid from a triacylglycerol (TG), thus generating free fatty acid (FFA) and diacylglycerol (DG). Alternative species forms of HSL, isoforms of HSL, fragments of HSL and variants of HSL, such as splice variants, allelic variants, alternate in frame exons, and alternative or premature termination or start sites, may be enzymatically or lipolytically active, e.g., capable of hydrolyzing triacylglycerol (TG). Lipolytic activity may be detected by assay methods known to those of skill in the art. Preferably, methods such as described hereinunder in Examples 1 and 2 are used. In a preferred embodiment of the invention, the method as described herein in paragraphs [0243] to [0247] in Example 2 herein, including references made therein, is used. A preferred embodiment of the invention includes measurement of lipase activity according to Jenkins et al. and Chung et al. as described in Example 2 herein. A further preferred embodiment of the invention includes measurement of lipase activity as described in paragraph [0246] in Example 2 herein and references made therein. A further preferred embodiment of the invention includes measurement of lipase activity as described in paragraph [0247] in Example 2 herein and references made therein. Any such assays and tests are described for the purpose of illustration and guidance; variations, alterations, adaptations and modifications will be obvious and possible tp the person of skill in the art. For instance, the test described in paragraphs [0246] or [0247] may be used to test the lipolytic activity and if desired the inhibition thereof by a given inhibitor, among others, of variants, fragments, variants due to premature termination or the like, of a lipase, preferably of ATGL lipase, without deviating from the scope of the invention.

The TARGET is preferably a lipase, more particularly ATGL, and particularly human ATGL. Exemplary human ATGL sequence is set out in FIG. 7 as well as in SEQ ID NO: 1 (amino acid sequence of human ATGL) and SEQ ID NO: 2 (cDNA including the coding sequence of human ATGL).

The term "cachexia and its associated or related disorders and conditions" or "cachexia and its related conditions or physiology" or variants thereof, refers to a disease or condition which involves, results at least in part from, or includes loss of weight, muscle atrophy, fatigue, weakness and significant loss of appetite in someone who is not actively trying to lose weight. It can be associated with or result from (directly or indirectly) various underlying disorders including cancer, metabolic acidosis (from decreased protein synthesis and increased protein catabolism), certain infectious diseases (e.g. tuberculosis, AIDS), some autoimmune disorders, addiction to drugs such as amphetamines or cocaine, chronic alcoholism and cirrhosis of the liver, chronic inflammatory disorders, anorexia, and neurodegenerative disease. In a particular aspect, cachexia is cancer cachexia. In other such aspects, muscle wasting and/or unintended body weight loss associated with neurological conditions, immobility or impaired mobility due to various diseases such as neurodegenerative disease, MS, spinal cord injury, is included in the term.

The term "alkyl" relates to a monovalent saturated aliphatic (i.e. non-aromatic) acyclic hydrocarbon group (i.e. a group consisting of carbon atoms and hydrogen atoms) which may be linear or branched and does not comprise any carbon-to-carbon double bond or any carbon-to-carbon triple bond.

The term "alkenyl" refers to a monovalent unsaturated aliphatic acyclic hydrocarbon group which may be linear or branched and comprises at least one carbon-to-carbon double bond while it does not comprise any carbon-to-carbon triple bond.

The term "alkynyl" refers to a monovalent unsaturated aliphatic acyclic hydrocarbon group which may be linear or branched and comprises at least one carbon-to-carbon triple bond and optionally one or more carbon-to-carbon double bonds.

The term "alkylene" refers to an alkanediyl group including straight chain and/or branched chain groups.

The term "alkenylene" refers to an alkenediyl group including straight chain and/or branched chain groups, and comprising at least one carbon-to-carbon double bond, while it does not comprise any carbon-to-carbon triple bond.

The term "alkynylene" refers to an alkynediyl group including straight chain and/or branched chain groups, and comprising at least one carbon-to-carbon triple bond and optionally one or more carbon-to-carbon double bonds.

The term "aryl" refers to a monovalent aromatic hydrocarbon group, including bridged ring and/or fused ring systems, containing at least one aromatic ring. "Aryl" may, for example, refer to phenyl, naphthyl or anthracenyl.

The term "heteroaryl" refers to a monocyclic or fused-ring polycyclic group having 5 to 14 ring atoms, having 6, 10 or 14 pi electrons shared in a cyclic array, and containing carbon ring atoms and 1, 2 or 3 hetero ring atom independently selected from O, N, or S. The term "heteroaryl" may, for example, relate to thiophenyl (thienyl), furanyl (furyl), pyrrolyl, imidazolyl, pyrazolyl, pyridinyl (pyridyl; including, e.g., 2-pyridyl, 3-pyridyl, and 4 pyridyl), pyrazinyl, pyrimidinyl, pyridazinyl, oxazolyl, isoxazolyl, or furazanyl.

The term "heteroaryl having 5 or 6 ring atoms, wherein 1, 2 or 3 ring atoms are each independently selected from oxygen, sulfur, or nitrogen and the other ring atoms are carbon atoms" refers to a monocyclic group having 5 or 6 ring atoms (i.e., ring members), having 6 pi electrons shared in a cyclic array, and containing carbon atoms and 1, 2 or 3 heteroatoms independently selected from O, N, or S, Non-limiting examples of heteroaryl groups include thiophenyl (thienyl), furanyl (furyl), pyrrolyl, imidazolyl, pyrazolyl, pyridinyl (pyridyl; including, e.g., 2-pyridyl, 3-pyridyl, and 4 pyridyl), pyrazinyl, pyrimidinyl, pyridazinyl, oxazolyl, isoxazolyl, and furazanyl.

The term "halogen" refers to fluoro, chloro, bromo, or iodo, and in particular to fluoro, chloro, or bromo.

Targets

The present invention is based on the present inventors' discovery that the TARGETS (e.g., ATGL and/or HSL, alternative species forms, isoforms, and variants as further described herein) are involved in cachexia and its associated disorders or conditions, whereby inhibition of the TARGETS results in correction, alleviation, or prevention of cachexia and its associated disorders or conditions or fat or muscle pathology. The present invention extends to the recognition that inhibition of lipase activity provides a novel approach to prevention, treatment and/or alleviation of cachexia, and its associated or related disorders and conditions, including weight loss, muscle atrophy or wasting, and reduction of WAT. Thus inhibition or reduction of the activity of TARGETS, particularly lipases, particularly inhibition of ATGL alone or in combination with inhibition of HSL, is provided for the prevention, treatment and/or alleviation of cachexia, and its associated or related disorders and conditions, including weight loss, muscle atrophy or wasting and reduction of WAT. The TARGETS are factors or protein molecules involved in the cachexia response and/or serve to facilitate, mediate, or otherwise participate such that their inhibition results in the alleviation, treatment and/or prevention of cachexia and its associated or related disorders and conditions, including weight loss, muscle atrophy or wasting and reduction of WAT. The TARGETS may also serve a role in correcting low body weight or fat or muscle atrophy associated with various conditions or disorders.

Lipase inhibitors, including pancreatic lipase inhibitors have been described and are known, although these are generally broad class inhibitors and may not be specific or particularly effective against the TARGET as described herein, particularly against ATGL. Known and/or recognized and described lipase inhibitors include but are not limited to: lipstatin and its saturated derivative Orlistat (Xenical®) which is described in U.S. Pat. No. 4,598,089; benzoquinone-derived compounds described in U.S. Pat. No. 7,355,055 B2; oxetanones or substituted β-lactones as described in U.S. Pat. No. 7,074,822, U.S. Pat. No. 6,852,865, U.S. Pat. No. 4,931,463, and U.S. Pat. No. 5,175,186; lipolytic enzyme inhibitors purothionins, protamines, polylysines described in U.S. Pat. No. 5,411,956 and U.S. Pat. No. 5,376,640; and thiophene compounds described in U.S. Pat. No. 7,064,122. Compounds with lipase-inhibiting activity, including these above as noted and referenced, and incorporated herein by reference, are described as suitable for the treatment and/or prophylaxis of obesity and of associated accompanying and/or concomitant diseases involved therewith, including in particular metabolic syndromes (hypertension, insulin resistance, Type II diabetes, hyperglyceridemia) and cardiovascular diseases (coronary heart disease, cerebrovascular disease, peripheral occlusive arterial disease). These compounds have been described as capable of reducing the proportion of edible fats actually digested by the body in the total edible fats ingested. These compounds are not described or suggested as involved in or mediating the prevention, alleviation or treatment of a pathological condition including cachexia, and its associated or related disorders and conditions, including weight loss, muscle atrophy or wasting and reduction of WAT. Therefore, the use of lipase inhibitors, including as described here above in the prevention, alleviation or treatment of a pathological condition including cachexia, and its associated or related disorders and conditions, including weight loss, muscle atrophy or wasting, reduction of WAT, is an aspect of the invention.

Therefore, in one aspect, the present invention relates to a method for assaying for drug candidate compounds that alleviate, prevent or treat cachexia and its associated disorders, conditions and/or physiology comprising contacting the compound with a polypeptide TARGET (e.g., ATGL and/or HSL, alternative species forms, isoforms, and variants as described herein above), or enzymatically active fragment thereof, under conditions that allow said polypeptide to bind to the compound or be modulated by the compound, and detecting the formation of a complex between the polypeptide and the compound or an alteration in the activity or expression of the polypeptide TARGET. In particular said method is used to identify an agent that inhibits the TARGET, particularly a lipase inhibitor, particularly and ATGL inhibitor. In particular said method may be used to identify drug candidate compounds that inhibit the excessive release of free FA from TG and/or lipolysis. One means of measuring the complex formation is to determine the binding affinity of said compound to said polypeptide. One means of measuring the alteration in the activity or expression of the polypeptide TARGET (e.g., ATGL and/or HSL, alternative species forms, isoforms, and variants as described herein above) is to determine the expression of the TARGET or the enzymatic activity of the TARGET or the release of the product(s) resulting from the enzymatic activity of the TARGET.

More particularly, the invention relates to a method for identifying an agent or compound that alleviates cachexia or its associated physiology whereby said agent or compound inhibits TARGET (e.g., ATGL and/or HSL, alternative species forms, isoforms, and variants as described herein above) said method comprising:

(a) contacting a population of mammalian cells with one or more compound that exhibits binding affinity for a TARGET (e.g., ATGL and/or HSL, alternative species forms, isoforms, and variants as described herein above) polypeptide, or fragment thereof, and
(b) measuring a compound-polypeptide property related to TG hydrolysis.

In a further aspect of the present invention said method is used to identify a compound that inhibits lipolysis, particularly inhibits ATGL activity or expression. In particular the inhibition of the release of free fatty acid from TG may be assessed.

In a further aspect, the present invention relates to a method for assaying for drug candidate compounds that alleviate cachexia and/or its physiology comprising contacting the compound with a polypeptide TARGET (e.g., ATGL and/or HSL, alternative species forms, isoforms, and variants as described herein above), or a fragment thereof, under conditions that allow said compound to modulate the activity or expression of the polypeptide, and determining the activity or expression of the polypeptide. In particular said method may be used to identify drug candidate compounds capable of suppressing the release of free fatty acid from TG. One particular means of measuring the activity or expression of the polypeptide is to determine the amount of said polypeptide using a polypeptide binding agent, such as an antibody, or to determine the activity of said polypeptide in a biological or biochemical measure, for instance the amount of lipolysis or TG hydrolysis.

The compound-polypeptide property referred to above is related to the expression and/or activity of the TARGET (e.g., ATGL and/or HSL, alternative species forms, isoforms, and variants as described herein above), and is a measurable phenomenon chosen by the person of ordinary skill in the art. The measurable property may be, for example, the binding affinity of said compound for a peptide domain of the polypeptide TARGET, a property related to the folding or activity of the disease-related protein or the level of any one of a number of biochemical marker levels of cachexia, fatty acids, or muscle wasting or atrophy. In a preferred method, TG hydrolysis is measured by measuring release of free fatty acid from a TG substrate.

In an additional aspect, the present invention relates to a method for assaying for drug candidate compounds that inhibit ATGL and/or HSL, comprising contacting the compound with a nucleic acid encoding a TARGET (e.g., ATGL and/or HSL, alternative species forms, isoforms, and variants as described herein above) polypeptide, or fragment thereof, under conditions that allow said nucleic acid to bind to or otherwise associate with the compound, and detecting the formation of a complex between the nucleic acid and the compound. In particular, said method may be used to identify drug candidate compounds able to suppress the release of inflammatory mediators from mast cells. One particular means of measuring the complex formation is to determine the binding affinity of said compound to said nucleic acid or the presence of a complex by virtue of resistance to nucleases or by gel mobility assays. Alternatively, complex formation may be determined by inhibition of nucleic acid transcription or translation.

Depending on the choice of the skilled artisan, the present assay method may be designed to function as a series of measurements, each of which is designed to determine whether the drug candidate compound is indeed acting on the TARGET (e.g., ATGL and/or HSL, alternative species forms, isoforms, and variants as described herein above) to thereby inhibit TG hydrolysis. For example, an assay designed to determine the binding affinity of a compound to the TARGET, or fragment thereof, may be necessary, but not sufficient, to ascertain whether the test compound would be useful for alleviating cachexia or its associated diseases, conditions or physiology when administered to a subject. Nonetheless, such binding information would be useful in identifying a set of test compounds for use in an assay that would measure a different property, further down the biochemical pathway, for example suppression of the body weight reduction in a cachexia model or infection model, such as AIDS.

Suitable controls should always be in place to insure against false positive readings. In a particular embodiment of the present invention the screening method comprises the additional step of comparing the compound to a suitable control. In one embodiment, the control may be a cell or a sample that has not been in contact with the test compound. In an alternative embodiment, the control may be a cell that does not express the TARGET (e.g., ATGL and/or HSL, alternative species forms, isoforms, and variants as described herein above); for example in one aspect of such an embodiment the test cell may naturally express the TARGET and the control cell may have been contacted with an agent, e.g. an siRNA, which inhibits or prevents expression of the TARGET. Alternatively, in another aspect of such an embodiment, the cell in its native state does not express the TARGET and the test cell has been engineered so as to express the TARGET, so that in this embodiment, the control could be the untransformed native cell. The control may also or alternatively utilize a known lipase inhibitor, including a broad or general lipase inhibitor. Whilst exemplary controls are described herein, and known in the art, this should not be taken as limiting; it is within the scope of a person of skill in the art to select appropriate controls for the experimental conditions being used.

The order of taking these measurements is not believed to be critical to the practice of the present invention, which may be practiced in any order. For example, one may first perform a screening assay of a set of compounds for which no information is known respecting the compounds' binding affinity for the TARGET (e.g., ATGL and/or HSL, alternative species forms, isoforms, and variants as described herein above) or capability of modulating the expression or activity of the TARGET. Alternatively, one may screen a set of compounds identified as having binding affinity for a TARGET protein domain, or a class of compounds identified as being an inhibitor of the TARGET. However, for the present assay to be meaningful to the ultimate use of the drug candidate compounds in cachexia or related diseases or physiology, a measurement of the stabilization of weight loss and/or inhibition of cachexia is necessary. Validation studies, including controls, and measurements of binding affinity to the polypeptides and/or specific or particular inhibition of the TARGET of the invention are nonetheless useful in identifying a compound useful in any therapeutic or diagnostic application.

Analogous approaches based on art-recognized methods and assays may be applicable with respect to the TARGETS (e.g., ATGL and/or HSL, alternative species forms, isoforms, and variants as described herein above) and compounds in any of various disease(s) characterized by body weight loss, fat loss, WAT reduction, muscle wasting or atrophy. An assay or assays may be designed to confirm that the test compound, having binding affinity for the TARGET or modulating the TARGET, inhibits the cachexia or its related conditions or physiology. In one such method the correction of body weight loss, fat loss, or muscle loss is measured.

The present assay method may be practiced in vitro, using one or more of the TARGET (e.g., ATGL and/or HSL, alternative species forms, isoforms, and variants as described herein above) proteins, or fragments thereof, including monomers, portions or subunits of polymeric proteins, peptides, oligopeptides and enzymatically active portions thereof.

The binding affinity of the compound with the TARGET (e.g., ATGL and/or HSL, alternative species forms, isoforms, and variants as described herein above) or a fragment thereof can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as $IC_{50}$ or $EC_{50}$. The $IC_{50}$ represents the concentration of a compound that is required for 50% inhibition of binding of another ligand to the polypeptide. The $EC_{50}$ represents the concentration required for obtaining 50% of the maximum effect in any assay that measures the TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, $IC_{50}$ and $EC_{50}$ values, i.e. in the range of 100 nM to 1 pM; a moderate to low affinity binding relates to a high Kd, $IC_{50}$ and $EC_{50}$ values, i.e. in the micromolar range.

The present assay method may also be practiced in a cellular assay. A host cell expressing the TARGET (e.g., ATGL and/or HSL, alternative species forms, isoforms, and variants as described herein above) can be a cell with endogenous expression or a cell over-expressing the TARGET e.g. by transduction. When the endogenous expression of the polypeptide is not sufficient to determine a baseline that can easily be measured, one may use host cells that over-express the TARGET. Over-expression has the advantage that the level of the TARGET substrate end products is higher than the activity level by endogenous expression. Accordingly, measuring such levels using presently available techniques is easier. In one such cellular assay, the biological activity of the TARGET may be measured by measuring the release of free FA from TG.

One embodiment of the present method for identifying a compound that inhibits cachexia, and its associated or related disorders and conditions, comprises culturing a population of mammalian cells expressing a TARGET (e.g., ATGL and/or HSL, alternative species forms, isoforms, and variants as described herein above) polypeptide, or a functional fragment or derivative thereof; determining a first level of FA release from TG or of ATGL activity or expression in said population of cells; exposing said population of cells to a compound, or a mixture of compounds; determining a second level of FA release from TG or of ATGL activity or expression in said population of cells under the same or commensurate conditions, during or after exposure of said population of cells to said compound, or the mixture of said compounds; and identifying the compound(s) that suppress TG hydrolysis and/or ATGL activity or expression. In a specific embodiment, the cells are adipose cells. In a specific embodiment the cells are human cells.

The release of FA from TG or lipolysis or lipase activity or ATGL activity can be determined by methods known in the art such as the methods as described herein.

The assay method may be based on the particular expression or activity of the TARGET (e.g., ATGL and/or HSL, alternative species forms, isoforms, and variants as described herein above) polypeptide, including but not limited to an enzyme activity. Thus, assays for the enzyme TARGETs may be based on enzymatic activity or enzyme expression. The measurable phenomenon, activity or property may be selected or chosen by the skilled artisan. The person of ordinary skill in the art may select from any of a number of assay formats, systems or design one using his knowledge and expertise in the art.

Specific methods to determine the inhibition by a compound by measuring the cleavage of the substrate by the polypeptide TARGET (e.g., ATGL and/or HSL, alternative species forms, isoforms, and variants as described herein above), which is a lipase, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

It should be understood that the cells expressing the polypeptides, may be cells naturally expressing the polypeptides, or the cells may be transfected to express the polypeptides, as described above. Also, the cells may be transduced to overexpress the polypeptide, or may be transfected to express a non-endogenous form of the polypeptide, which can be differentially assayed or assessed.

In one particular embodiment the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of the release of FA from TG. In a particular embodiment, the cells used in the present method are mammalian adipose cells.

In a particular aspect of the present invention the methods include the additional step of comparing the compound to be tested to a control, where the control is a population of cells that have not been contacted with the test compound. In a particular aspect of the present invention the methods described above include the additional step of comparing the compound to be tested to a control, where the control is a population of cells that do not express said polypeptide.

In a particular aspect of the present invention the methods described above include the additional step of comparing the compound to be tested to a control, where the control is a general lipase inhibitor such as a pancreatric lipase inhibitor.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich, BioFocus DPI) or natural compound libraries (Specs, TimTec).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al. (1997) Adv Drug Del Rev 23: 3-25). Peptides comprise another preferred class of drug candidate compounds. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound.

Another preferred class of drug candidate compounds is an antibody. The present invention also provides antibodies directed against the TARGETS (e.g., ATGL and/or HSL, alternative species forms, isoforms, and variants as described herein above). These antibodies may be endogenously produced to bind to the TARGETS within the cell, or added to the tissue to bind to the TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET (e.g., ATGL and/or HSL, alternative species forms, isoforms, and variants as described herein above) protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boerner, et al. are also available for the preparation of human monoclonal antibodies (Cole, et al.

(1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGETS (e.g., ATGL and/or HSL, alternative species forms, isoforms, and variants as described herein above). The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In one such embodiment, one of the binding specificities is for one domain of the TARGET (e.g., ATGL and/or HSL, alternative species forms, isoforms, and variants as described herein above); the other one is for another domain of the TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method uses a drug candidate compound identified as having a binding affinity for the TARGET (e.g., ATGL and/or HSL, alternative species forms, isoforms, and variants as described herein above), and/or has already been identified as having down-regulating activity such as antagonist activity for the TARGET.

In vivo animal models of cachexia or wasting conditions or infections or other disorders wherein body weight loss or muscle atrophy is seen may be utilized by the skilled artisan to further or additionally screen, assess, and/or verify the agents or compounds identified in the present invention, including further assessing TARGET modulation in vivo. Such animal models include, but are not limited to cachexia models, cancer or tumor models, AIDS models.

The present invention further relates to a method for inhibiting lipolysis, particularly inhibiting cachexia, comprising contacting said cells with an expression inhibitory agent comprising a polynucleotide sequence that complements at least about 15 to about 30, particularly at least 17 to about 30, most particularly at least 17 to about 25 contiguous nucleotides of a nucleotide sequence encoding a polypeptide TARGET or portion thereof including the TARGET ATGL sequences set out herein and in FIG. 7 (human ATGL; SEQ ID NO: 1 shows the amino acid sequence and SEQ ID NO: 2 shows the cDNA including the coding sequence) and 8 (mouse ATGL; SEQ ID NO: 3 shows the amino acid sequence and SEQ ID NO: 4 shows the cDNA including the coding sequence).

Another aspect of the present invention relates to a method for modulating cachexia or associated disorders, conditions or physiology in a mammal, comprising contacting said mammal with an expression-inhibiting agent that inhibits the translation in the cell of a polyribonucleotide encoding the TARGET (e.g., ATGL and/or HSL, alternative species forms, isoforms, and variants as described herein above). A particular embodiment relates to a composition comprising a polynucleotide including at least one antisense strand that functions to pair the agent with the TARGET mRNA, and thereby down-regulate or block the expression of the TARGET. The inhibitory agent preferably comprises antisense polynucleotide, a ribozyme, and a small interfering RNA (siRNA), wherein said agent comprises a nucleic acid sequence complementary to, or engineered from, a naturally-occurring polynucleotide sequence encoding a portion of a polypeptide TARGET, including ATGL as set out in FIG. 7 (human ATGL; SEQ ID NO: 1 shows the amino acid sequence and SEQ ID NO: 2 shows the cDNA including the coding sequence) or 8 (mouse ATGL; SEQ ID NO: 3 shows the amino acid sequence and SEQ ID NO: 4 shows the cDNA including the coding sequence), or as known in the art.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding the TARGET (e.g., ATGL and/or HSL, alternative species forms, isoforms, and variants as described herein above) or the corresponding messenger RNA. In addition, antisense nucleic acids may be designed which decrease expression of the nucleic acid sequence capable of encoding the TARGET by inhibiting splicing of its primary transcript. Any length of antisense sequence is suitable for practice of the invention so long as it is capable of down-regulating or blocking expression of a nucleic acid coding for the TARGETS. Preferably, the antisense sequence is at least about 17 nucleotides in length. The preparation and use of antisense nucleic acids, DNA encoding antisense RNAs and the use of oligo and genetic antisense is known in the art.

The skilled artisan can readily utilize any of several strategies to facilitate and simplify the selection process for antisense nucleic acids and oligonucleotides effective in inhibition of TARGET (e.g., ATGL and/or HSL, alternative species forms, isoforms, and variants as described herein above) expression and/or inhibition of cachexia or related conditions or physiology. Predictions of the binding energy or calculation of thermodynamic indices between an olionucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). Schmidt and Thompson (U.S. Pat. No. 6,416,951) describe a method for identifying a functional antisense agent comprising hybridizing an RNA with an oligonucleotide and measuring in real time the kinetics of hybridization by hybridizing in the presence of an intercalation dye or incorporating a label and measuring the spectroscopic properties of the dye or the label's signal in the presence of unlabelled oligonucleotide. In addition, any of a variety of computer programs may be utilized which predict suitable antisense oligonucleotide sequences or antisense targets utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.). In addition, antisense oligonucleotides suitable in the present invention may be identified by screening an oligonucleotide library, or a library of nucleic acid molecules, under hybridization conditions and selecting for those which hybridize to the target RNA or nucleic acid (see for example U.S. Pat. No. 6,500,615). Mishra and Toulme have also developed a selection procedure based on selective amplification of oligonucleotides that bind target (Mishra et al (1994) Life Sciences 317:977-982). Oligonucleotides may also be selected by their ability to mediate cleavage of target RNA by RNAse H, by selection and characterization of the cleavage fragments (Ho et al (1996) Nucl Acids Res 24:1901-1907; Ho et al (1998) Nature Biotechnology 16:59-630). Generation and targeting of oligonucleotides to GGGA motifs of RNA molecules has also been described (U.S. Pat. No. 6,277,981).

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (RNase) H, which cleaves the mRNA component of the hybrid molecule. Oligonucleotides may also contain one or more substituted sugar moieties. Particular oligonucleotides comprise one of the following at the 2' position: OH, SH, $SCH_3$, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2'-deoxy, O-pentoxy, O-propoxy. O-methoxy, fluoro, methoxyethoxy phosphorothioates, modified bases, as well as other modifications known to those of skill in the art.

Another type of expression-inhibitory agent that can reduce the level of the TARGETS (e.g., ATGL and/or HSL, alternative species forms, isoforms, and variants as described herein above) is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base pairing. Once it is bound to the correct target site, the ribozyme acts enzymatically to cut the target mRNA. Cleavage of the mRNA by a ribozyme destroys its ability to direct synthesis of the corresponding polypeptide. Once the ribozyme has cleaved its target sequence, it is released and can repeatedly bind and cleave at other mRNAs.

Ribozyme forms include a hammerhead motif a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the target mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

Analogous to antisense RNA, the siRNA can be modified to confer resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage of the siRNA to one or more moieties or conjugates. The nucleotide sequences are selected according to siRNA designing rules that give an improved reduction of the TARGET (e.g., ATGL and/or HSL, alternative species forms, isoforms, and variants as described herein above) sequences compared to nucleotide sequences that do not comply with these siRNA designing rules (For a discussion of these rules and examples of the preparation of siRNA, WO 2004/094636, and US 2003/0198627, are hereby incorporated by reference).

The present invention also relates to compositions, and methods using said compositions, comprising a DNA expression vector capable of expressing a polynucleotide capable of stabilizing adipose cells or tissue, or muscle mass, in particular capable of inhibiting unintended loss of adipose tissue or muscle mass, and described hereinabove as an expression inhibition agent.

A particular aspect of these compositions and methods relates to the down-regulation or blocking of the expression of the TARGET (e.g., ATGL and/or HSL, alternative species forms, isoforms, and variants as described herein above) by the induced expression of a polynucleotide encoding an intracellular binding protein that is capable of selectively interacting with the TARGET. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of a TARGET. More preferably, the intracellular binding protein is a single chain antibody.

The polynucleotide expressing the expression-inhibiting agent, or a polynucleotide expressing the TARGET (e.g., ATGL and/or HSL, alternative species forms, isoforms, and variants as described herein above) polypeptide in cells, is particularly included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaiviral vector systems, and all may be used to introduce and express polynucleotide sequence for the expression-inhibiting agents or the polynucleotide expressing the TARGET polypeptide in the target cells.

Particularly, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US 2003/0180258 and US 2004/0071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus") MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_r$, $P_1$, and trp promoters. Among the eukaryotic (including viral) promoters useful for practice of this invention are ubiquitous promoters (e.g. HPRT, vimentin, actin, tubulin), therapeutic gene promoters (e.g. MDR type, CFTR, factor VIII), tissue-specific promoters, including animal transcriptional control regions, which exhibit tissue specificity and have been utilized in transgenic animals, e.g. chymase gene control region which is active in mast cells (Liao et al., (1997), Journal of Biological Chemistry, 272: 2969-2976), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), and beta-globin gene control region which is active in myeloid cells (Mogram, et al. (1985) Nature 315:338-40; Kollias, et al. (1986) Cell 46:89-94).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Further promoters which may be of use in the practice of the invention include promoters which are active and/or expressed in lipase expressing cells, ATGL expressing cells, adipocytes, hepatocytes.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et. al. (1987) Proc. Natl. Acad Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263: 14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, cachexia inhibiting or modulating compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET (e.g., ATGL and/or HSL, alternative species forms, isoforms, and variants as described herein above); a nucleic acid would be able to replicate, translate a message, or hybridize to a complementary mRNA of the TARGET; a vector would be able to transfect a target cell and express the antisense, antibody, ribozyme or siRNA as described hereinabove; an antibody would bind a the TARGET polypeptide domain.

A particular biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particular embodiment of the present composition invention is a pharmaceutical composition comprising a therapeutically effective amount of an expression-inhibiting agent as described hereinabove, in admixture with a pharmaceutically acceptable carrier. Another particular embodiment is a pharmaceutical composition for the treatment or prevention of a disease or condition involving cachexia, and its associated or related disorders and conditions, or a susceptibility to such conditions, comprising an effective amount of the TARGET (e.g., ATGL and/or HSL, alternative species forms, isoforms, and variants as described herein above) antagonist or inverse agonist, its pharmaceutically acceptable salts, hydrates, solvates, or prodrugs thereof in admixture with a pharmaceutically acceptable carrier. A further particular embodiment is a pharmaceutical composition for the treatment or prevention of a disease or condition involving cachexia, or a susceptibility to the condition, comprising an effective amount of the TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The agents or compositions of the invention may be combined for administration with or embedded in polymeric carrier(s), biodegradable or biomimetic matrices or in a scaffold. The carrier, matrix or scaffold may be of any material that will allow composition to be incorporated and expressed and will be compatible with the addition of cells or in the presence of cells. Particularly, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally-occurring biodegradable materials. It may be preferable to sterilize the matrix or scaffold material prior to administration or implantation, e.g., by treatment with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof. Matrices suitable include a polymeric mesh or sponge and a polymeric hydrogel. In the particular embodiment, the matrix is biodegradable over a time period of less than a year, more particularly less than six months, most particularly over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.). In general, these polymers are at least partially soluble in aqueous solutions, such as water, buffered salt solutions, or aqueous alcohol solutions that have charged side groups, or a monovalent ionic salt thereof.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a vector encoding an agent of the present invention, particularly a recombinant replication defective vector, and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

In a further aspect the present invention provides a method of preventing and/or treating cachexia, and its associated or related disorders and conditions, including weight loss, muscle atrophy or wasting, reduction of WAT, and reduction of fat, said method comprising administering to a subject a therapeutically effective amount of an agent as disclosed herein. In a particular embodiment, the agent is selected from an expression-inhibiting agent and an antibody.

The invention also relates to the use of an agent as described above for the preparation of a medicament for treating or preventing cachexia, and its associated or related disorders and conditions, including weight loss, muscle atrophy or wasting, and reduction of WAT. In a particular embodiment, the disease is cancer cachexia, wasting disease associated with AIDS or other infectious disease or condition, chronic substance abuse, alcoholism, cirrhosis of the liver or low body weight associated with anorexia or other disorders.

The present invention also provides a method of treating and/or preventing cachexia, and its associated or related disorders and conditions, including weight loss, muscle atrophy or wasting, and reduction of WAT, a pharmaceutical composition or compound as described herein, particularly a therapeutically effective amount of an agent which inhibits the expression or activity of a TARGET (e.g., ATGL and/or HSL, alternative species forms, isoforms, and variants as described herein above) as identified herein. In a particular embodiment, the disease is cancer cachexia, wasting disease associated with AIDS or other infectious disease or condition, chronic substance abuse, alcoholism, cirrhosis of the liver, or low body weight associated with anorexia or other disorders.

The invention also relates to an agent or a pharmaceutical composition as described above for use in the treatment and/or prevention of cachexia, and its associated or related disorders and conditions, including weight loss, muscle atrophy or wasting and reduction of WAT.

Administration of the agent or pharmaceutical composition of the present invention to the subject patient includes both self-administration and administration by another person. The patient may be in need of treatment for an existing disease or medical condition, or may desire prophylactic treatment to prevent or reduce the risk for diseases and medical conditions characterized by cachexia, and its associated or related disorders and conditions. The agent of the present invention may be delivered to the subject patient orally, transdermally, via inhalation, injection, nasally, rectally or via a sustained release formulation.

Still another aspect of the invention relates to a method for diagnosing a pathological condition including cachexia, and its associated or related disorders and conditions, including weight loss, muscle atrophy or wasting and reduction of WAT, comprising determining the amount or activity of a polypeptide TARGET (e.g., ATGL and/or HSL, alternative species forms, isoforms, and variants as described herein above) in a biological sample, and comparing the amount with the amount of the polypeptide in a healthy subject, wherein an increase of the amount of or activity of polypeptide compared to the healthy subject is indicative of the presence of the pathological condition. In a particular embodiment, the disease is cancer cachexia, wasting disease associated with AIDS or other infectious disease or condition, substance abuse, chronic alcoholism, cirrhosis of the liver or low body weight associated with anorexia or other disorders.

Another aspect of the invention relates to a method for diagnosing a pathological condition including cachexia, and its associated or related disorders and conditions, including weight loss, muscle atrophy or wasting and reduction of WAT, comprising determining the amount, expression, or activity of a ATGL in a biological sample, and comparing the amount with the amount of the polypeptide in a healthy subject, wherein an increase of the amount of or activity of or expression of ATGL compared to the healthy subject is indicative of the presence of the pathological condition. In a particular embodiment, the disease is cancer cachexia, wasting disease associated with AIDS or other infectious disease or condition, substance abuse, chronic alcoholism, cirrhosis of the liver or low body weight associated with anorexia or other disorders.

The polypeptides or the polynucleotides of the present invention employed in the methods described herein may be free in solution, affixed to a solid support, borne on a cell surface, or located intracellularly. To perform the methods it is feasible to immobilize either the polypeptide of the present invention or the compound to facilitate separation of complexes from uncomplexed forms of the polypeptide, as well as to accommodate automation of the assay. Interaction (e.g., binding) of the polypeptide of the present invention with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the polypeptide of the present invention can be "His" tagged, and subsequently adsorbed onto Ni-NTA microtitre plates, or ProtA fusions with the polypeptides of the present invention can be adsorbed to IgG, which are then combined with the cell lysates (e.g., ($^{35}$)S-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the protein of the present invention quantitated from the gel using standard electrophoretic techniques.

Other techniques for immobilizing protein on matrices can also be used in the method of identifying compounds. For example, either the polypeptide of the present invention or the compound can be immobilized utilizing conjugation of biotin and streptavidin. Biotinylated protein molecules of the present invention can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptides of the present invention but which do not interfere with binding of the polypeptide to the compound can be derivatized to the wells of the plate, and the polypeptide of the present invention can be trapped in the wells by antibody conjugation. As described above, preparations of a labeled candidate compound are incubated in the wells of the plate presenting the polypeptide of the present invention, and the amount of complex trapped in the well can be quantitated.

The polynucleotides encoding the TARGET polypeptides include ATGL and HSL encoding polynucleotides, particularly ATGL encoding nucleotides, such as human or mouse ATGL as known in the art and/or set out herein in FIG. 7 (human ATGL; SEQ ID NO: 1 shows the amino acid sequence and SEQ ID NO: 2 shows the cDNA including the coding sequence) and 8 (mouse ATGL; SEQ ID NO: 3 shows the amino acid sequence and SEQ ID NO: 4 shows the cDNA including the coding sequence).

The present invention further provides a compound of formula (I)

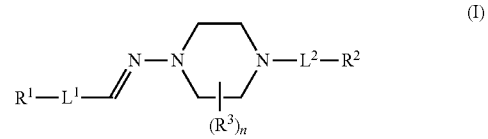

or a pharmaceutically acceptable salt, solvate or prodrug thereof, for use in the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

$L^1$ is a bond, $C_{1-10}$ alkylene, $C_{2-10}$ alkenylene, or $C_{2-10}$ alkynylene. Said alkylene, said alkenylene or said alkynylene is optionally substituted with one or more (such as, e.g., one, two, three, or four), preferably one or two, more preferably one, groups independently selected from halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl). Most preferably, said alkylene, said alkenylene or said alkynylene is unsubstituted. Furthermore, one or more (such as, e.g., one, two, three, or four), preferably one or two, more preferably one, —CH$_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —SO$_2$—, preferably selected from —O—, —NH—, —N($C_{1-4}$ alkyl)-, or —S—, and more preferably selected from —O— or —S—. If more than one —CH$_2$— unit is replaced, then it is preferred that the replaced —CH$_2$— units are non-adjacent. Most preferably, no —CH$_2$— units are replaced.

Preferably, $L^1$ is a bond or $C_{1-4}$ alkylene, wherein one —CH$_2$— unit comprised in said alkylene is optionally replaced by —O—. More preferably, $L^1$ is a bond.

$L^2$ is a bond, $C_{1-10}$ alkylene, $C_{2-10}$ alkenylene, or $C_{2-10}$ alkynylene. Said alkylene, said alkenylene or said alkynylene is optionally substituted with one or more (such as, e.g., one, two, three, or four), preferably one or two, more preferably one, groups independently selected from halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl). Most preferably, said alkylene, said alkenylene or said alkynylene is unsubstituted. Furthermore, one or more (such as, e.g., one, two, three, or four), preferably one or two, more preferably one, —CH$_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —SO$_2$—, preferably selected from —O—, —NH—, —N($C_{1-4}$ alkyl)-, or —S—, and more preferably selected from —O— or —S—. If more than one —CH$_2$— unit is replaced, then it is preferred that the replaced —CH$_2$— units are non-adjacent. Most preferably, no —CH$_2$— units are replaced.

Preferably, $L^2$ is a bond or $C_{1-4}$ alkylene, wherein one —CH$_2$— unit comprised in said alkylene is optionally replaced by —O—. More preferably, $L^2$ is a bond.

$R^1$ is optionally substituted aryl or optionally substituted heteroaryl, wherein said aryl or said heteroaryl may be substituted with one or more (such as, e.g., one, two, three, or four), preferably one or two, groups independently selected from $C_{1-4}$ alkyl, halogen, —CF$_3$, —CN, —OH, —O($C_{1-4}$ alkyl), —NH₂, —NH(C₁₋₄ alkyl), or —N(C₁₋₄ alkyl)(C₁₋₄ alkyl). Preferably, said aryl is selected from phenyl or naphthyl; more preferably, said aryl is phenyl. Preferably, said heteroaryl has 5 or 6 ring atoms, wherein 1, 2, or 3 ring atoms are each independently selected from oxygen, sulfur, or nitrogen and the other ring atoms are carbon atoms. For example, said heteroaryl may be selected from pyridinyl, thienyl, furyl, pyrrolyl, imidazolyl, pyrazolyl, pyrazinyl, pyrimidinyl, pyridazinyl, oxazolyl, isoxazolyl, or furazanyl.

Preferably, $R^1$ is optionally substituted phenyl, wherein said phenyl may be substituted with one or more, preferably one or two, groups independently selected from $C_{1-4}$ alkyl, halogen, —CF₃, —CN, —OH, —O($C_{1-4}$ alkyl), —NH₂, —NH($C_{1-4}$ alkyl), or —N($C_{1-4}$ alkyl)($C_{1-4}$ alkyl).

$R^2$ is optionally substituted aryl or optionally substituted heteroaryl, wherein said aryl or said heteroaryl may be substituted with one or more (such as, e.g., one, two, three, or four), preferably one or two, groups independently selected from $C_{1-4}$ alkyl, halogen, —CF₃, —CN, —OH, —O($C_{1-4}$ alkyl), —NH₂, —NH($C_{1-4}$ alkyl), or —N($C_{1-4}$ alkyl)($C_{1-4}$ alkyl). Preferably, said aryl is selected from phenyl or naphthyl; more preferably, said aryl is phenyl. Preferably, said heteroaryl has 5 or 6 ring atoms, wherein 1, 2, or 3 ring atoms are each independently selected from oxygen, sulfur, or nitrogen and the other ring atoms are carbon atoms. For example, said heteroaryl may be selected from pyridinyl, thienyl, furyl, pyrrolyl, imidazolyl, pyrazolyl, pyrazinyl, pyrimidinyl, pyridazinyl, oxazolyl, isoxazolyl, or furazanyl.

Preferably, $R^2$ is optionally substituted phenyl, wherein said phenyl may be substituted with one or more, preferably one or two, groups independently selected from $C_{1-4}$ alkyl, halogen, —CF₃, —CN, —OH, —O($C_{1-4}$ alkyl), —NH₂, —NH($C_{1-4}$ alkyl), or —N($C_{1-4}$ alkyl)($C_{1-4}$ alkyl).

n is an integer of 0 to 8. Preferably, n is 0, 1, 2, 3, or 4. More preferably, n is 0, 1 or 2. Most preferably, n is 0.

It is to be understood that, when n is 0, the carbon ring atoms and the nitrogen ring atoms of the piperazine moiety of the compound of formula (I) are not further substituted, i.e. the carbon ring atoms of the piperazine moiety are substituted with hydrogen and the nitrogen ring atoms of the piperazine moiety carry a lone electron pair.

Each $R^3$ is independently selected from $C_{1-4}$ alkyl, halogen, —CF₃, —CN, —OH, —O($C_{1-4}$ alkyl), —NH₂, —NH ($C_{1-4}$ alkyl), or —N($C_{1-4}$ alkyl)($C_{1-4}$ alkyl).

Preferably, each $R^3$ is attached to a carbon atom of the piperazine moiety. More preferably, each $R^3$ is attached to a different carbon atom of the piperazine moiety and n is an integer of 0, 1, 2, 3, or 4 (preferably, 0, 1, or 2).

A particularly preferred compound of formula (I) is "compound 4" as described in Example 3, i.e. a compound having the following formula

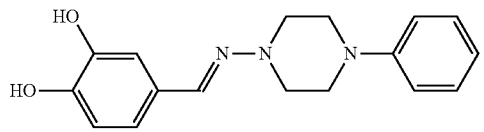

or a pharmaceutically acceptable salt, solvate or prodrug thereof.

Moreover, the present invention provides a compound of formula (II)

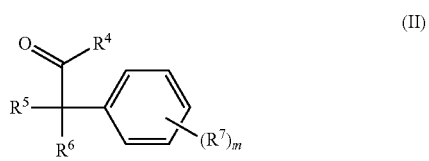

or a pharmaceutically acceptable salt, solvate or prodrug thereof for use in the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

$R^4$ is selected from —OH, —O($C_{1-4}$ alkyl), —NH₂, —NH ($C_{1-4}$ alkyl), —N($C_{1-4}$ alkyl)($C_{1-4}$ alkyl), —SH, or —S($C_{1-4}$ alkyl).

Preferably, $R^4$ is selected from —OH or —O($C_{1-4}$ alkyl).

$R^5$ and $R^6$ are each independently selected from $C_{1-4}$ alkyl, halogen, —CF₃, —CN, —OH, —O($C_{1-4}$ alkyl), —NH₂, —NH($C_{1-4}$ alkyl), or —N($C_{1-4}$ alkyl)($C_{1-4}$ alkyl).

It is preferred that $R^5$ is —OH or —O($C_{1-4}$ alkyl), in particular —OH. Furthermore, it is preferred that $R^6$ is halogen, —CF₃, or —CN, in particular —CF₃.

m is an integer of 0 to 5. Preferably, m is 0, 1, 2, or 3. In a preferred embodiment, m is 3.

It is to be understood that, when m is 0, the carbon ring atoms of the phenyl moiety of the compound of formula (II) are not further substituted, i.e. they are substituted with hydrogen.

Each $R^7$ is independently selected from $C_{1-4}$ alkyl, halogen, —CF₃, —CN, —OH, —O($C_{1-4}$ alkyl), —NH₂, —NH ($C_{1-4}$ alkyl), or —N($C_{1-4}$ alkyl)($C_{1-4}$ alkyl).

A particularly preferred compound of formula (II) is "compound 3" as described in Example 3, or a compound having the following formula

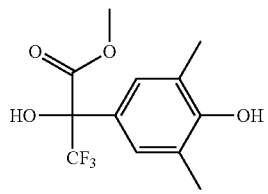 [SMILES: COC(=O)C(O)(c1cc(C)c(O)c(C)c1)C(F)(F)F]

or a pharmaceutically acceptable salt, solvate or prodrug thereof.

The invention further provides a compound of formula (III)

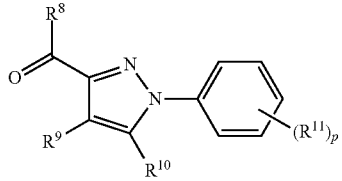

(III)

or a pharmaceutically acceptable salt, solvate or prodrug thereof, for use in the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

$R^8$ is selected from —OH, —O($C_{1-4}$ alkyl), —NH$_2$, —NH($C_{1-4}$ alkyl), —N($C_{1-4}$ alkyl)($C_{1-4}$ alkyl), —SH, or —S($C_{1-4}$ alkyl).

Preferably, $R^8$ is selected from —OH or —O($C_{1-4}$ alkyl).

$R^9$ and $R^{10}$ are each independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl).

It is preferred that $R^9$ is —OH or —O($C_{1-4}$ alkyl), in particular —OH. Furthermore, it is preferred that $R^{10}$ is hydrogen.

p is an integer of 0 to 5. Preferably, p is 0, 1, 2, or 3. In a preferred embodiment, p is 3.

It is to be understood that, when p is 0, the carbon ring atoms of the phenyl moiety of the compound of formula (III) are not further substituted, i.e. they are substituted with hydrogen.

Each $R^{11}$ is independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl).

In a preferred embodiment, p is 1 and $R^{11}$ is selected from —OH or —O($C_{1-4}$ alkyl).

A particularly preferred compound of formula (III) is "compound 9" as described in Example 3, i.e. a compound having the following formula

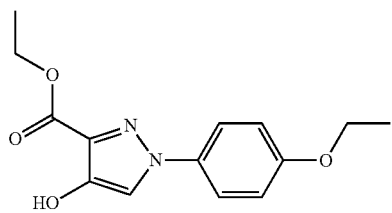 [SMILES: CCOC(=O)c1nn(-c2ccc(OCC)cc2)cc1O]

or a pharmaceutically acceptable salt, solvate or prodrug thereof.

Furthermore, the present invention provides a compound of formula (IV)

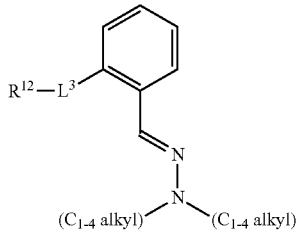

(IV)

or a pharmaceutically acceptable salt, solvate or prodrug thereof, for use in the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

$L^3$ is a bond, $C_{1-10}$ alkylene, $C_{2-10}$ alkenylene, or $C_{2-10}$ alkynylene. Said alkylene, said alkenylene or said alkynylene is optionally substituted with one or more (such as, e.g., one, two, three, or four), preferably one or two, more preferably one, groups independently selected from halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl). Most preferably, said alkylene, said alkenylene or said alkynylene is unsubstituted. Furthermore, one or more (such as, e.g., one, two, three, or four), preferably one or two, more preferably one, —CH$_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —CO—O—, —O—CO—, —S—, —SO—, or —SO$_2$—, preferably selected from —CO—NH—, —NH—CO—, —CO—O—, or —O—CO—, and more preferably selected from —CO—O— or —O—CO—.

Preferably, $L^3$ is selected from —O—, —NH—, —N($C_{1-4}$ alkyl)-, —CO—, —CO—NH—, —NH—CO—, —CO—O—, —O—CO—, —S—, —SO—, or —SO$_2$—. More preferably, $L^3$ is selected from —CO—NH—, —NH—CO—, —CO—O—, or —O—CO—. Most preferably, $L^3$ is selected from —CO—O— or —O—CO—.

$R^{12}$ is optionally substituted aryl or optionally substituted heteroaryl, wherein said aryl or said heteroaryl may be substituted with one or more (such as, e.g., one, two, three, or four), preferably one or two, groups independently selected from $C_{1-4}$ alkyl, halogen, —CF$_3$, —CN, —OH, —O($C_{1-4}$ alkyl), —NH$_2$, —NH($C_{1-4}$ alkyl), or —N($C_{1-4}$ alkyl)($C_{1-4}$ alkyl). Said aryl or said heteroaryl is preferably unsubstituted. Preferably, said aryl is selected from phenyl or naphthyl; more preferably, said aryl is phenyl. Preferably, said heteroaryl has 5 or 6 ring atoms, wherein 1, 2, or 3 ring atoms are each independently selected from oxygen, sulfur, or nitrogen and the other ring atoms are carbon atoms. For example, said heteroaryl may be selected from pyridinyl, thienyl, furyl, pyrrolyl, imidazolyl, pyrazolyl, pyrazinyl, pyrimidinyl, pyridazinyl, oxazolyl, isoxazolyl, or furazanyl. In a preferred embodiment, said heteroaryl is pyridinyl (e.g., pyridin-3-yl).

Preferably, $R^{12}$ is optionally substituted heteroaryl having 5 or 6 ring atoms, wherein 1, 2, or 3 ring atoms are each independently selected from oxygen, sulfur, or nitrogen and the other ring atoms are carbon atoms. Said heteroaryl may be substituted with one or more, preferably one or two, groups independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl). It is preferred that said heteroaryl is pyridinyl.

A particularly preferred compound of formula (IV) is "compound 7" as described in Example 3, i.e. a compound having the following formula

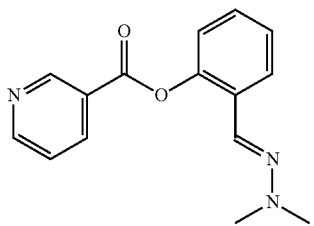 [SMILES: CN(C)/N=C/c1ccccc1OC(=O)c1cccnc1]

or a pharmaceutically acceptable salt, solvate or prodrug thereof.

The compounds of formula (I), (II), (III) or (IV) as described and defined herein above, and also the compounds described in Example 3 (e.g., Compound 3 (0875-0003-7167), Compound 4 (0875-0003-6659), Compound 5 (0876-0001-1449), Compound 7 (0875-0003-7401), Compound 8 (0875-0003-7306), or Compound 9 (0875-0003-7092)) can furthermore be used as ATGL inhibitors.

The present invention further relates to a pharmaceutical composition comprising a compound as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), in combination with a pharmaceutically acceptable excipient for use in the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

The invention also encompasses the use of a compound as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), for the preparation of a medicament for the treatment or prevention of cachexia, or its associated or related disorders or conditions, including e.g. weight loss, muscle atrophy or wasting, fat loss, and/or reduced WAT. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

Furthermore, the present invention relates to a method for treating or preventing cachexia, or its associated or related disorders or conditions, including e.g. weight loss, muscle atrophy or wasting, fat loss, and/or reduced WAT, the method comprising the administration of a compound as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), or a pharmaceutical composition, the pharmaceutical composition comprising any of the aforementioned compounds and a pharmaceutically acceptable excipient, to a subject (preferably a human) in need of such a treatment or prevention. In a particular embodiment, said cachexia or an associated or related disorder or condition thereof is cancer cachexia, wasting disease associated with AIDS or other infectious disease or condition, chronic substance abuse, alcoholism, cirrhosis of the liver or low body weight associated with anorexia or other disorders.

The compounds according to the present application, including the compounds of formula (I), (II), (III) or (IV) as described and defined herein above and the compounds described in Example 3, can be prepared by various ways which are known in the art and will be readily apparent to a person skilled in the field of synthetic chemistry.

Furthermore, the compounds described in Example 3 can be ordered from: ChemDiv, Inc. ("ChemDiv"), 6605 Nancy Ridge Drive, San Diego, Calif. 92121, USA (world wide web at chemdiv.com); or ASINEX Ltd. ("Asinex"), 20 Geroev Panfilovtzev Str. Bldg 1, Moscow 125480, Russia (world wide web at asinex.com). In particular, compounds 2, 3, 4, 6, 7, 8, and 9 as described in Example 3 can be obtained from ChemDiv; their ChemDiv supplier's ID numbers are indicated in Example 3. Compound 5 as described in Example 3 can be obtained from Asinex; its Asinex compound ID number is indicated in Example 3. The compounds according to the invention may further be obtained from eMolecules, Inc., 380 Stevens Ave #311, Solana Beach, Calif. 92075, USA.

The scope of the invention embraces all pharmaceutically acceptable salt forms of the compound as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compound as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Furthermore, the formulas in the present application are intended to cover all possible stereoisomers, including enantiomers and diastereomers, of the indicated compounds.

Thus, all stereoisomers of the compounds of the present invention are contemplated as part of the present invention, either in admixtures or in pure or substantially pure form. The scope of the compounds according to the invention embraces all the possible stereoisomers and their mixtures. It very particularly embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

Pharmaceutically acceptable prodrugs of compounds as described and defined herein, in particular a compound of formula (I), (II), (III) or (IV), or a compound as described in Example 3 (e.g., Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), or Compound 9 (0875-0003-7092)), are derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propyl ester, isopropylester, n-butylester, isobutylester, tert-butylester, morpholinoethylester, N,N-diethylglycolamidoester or α-acetoxyethylester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

The invention is further illustrated in the following examples.

EXPERIMENTAL SECTION

Example 1

Animal Model Studies

A murine animal model of tumor associated cachexia was utilized to examine the role of lipases in cachexia. Lewis lung carcinoma cells are used in mice to generate tumors and cachexia effects. Lewis lung carcinoma cells were obtained from the European Collection of Cell Cultures (ECACC) and maintained in cell culture before injecting ~4×10$^6$ cells subcutaneously in the neck area of C57BL/6J mice Lewis lung carcinoma is a cell line established from the lung of a C57BL mouse bearing a tumor resulting from an implantation of primary Lewis lung carcinoma. The cells are reported to be highly tumorigenic, but weakly metastatic in mice (Laster, W. R. et al (1971) Proc of the Amer Assoc for Cancer Research 12(NMAR):7). Average tumor weight after 21 days in this model was 3.67 g. Numerous mitoses seen in HE stained histological sections indicated a highly proliferating tumor in the mice. Average mouse body weight, however, decreased by 3.0 g after 21 days. In this model system, tumor bearing wild type animals lose on average 3.84 g in body weight (excluding the tumor) whereas wild type animals without tumor gain 2.2 g in the same time period (20 days). The difference is highly significant.

Knockouts were generated in mice for both ATGL (Lipase A) and for HSL (Lipase B), using the method as previously reported (Haemmerle, G et al (2006) Science 312(5774):734-737; Schweiger, M et al (2006) J Biol Chem 281(52):40236-40241). Lewis lung carcinoma cells were injected ~4×10$^6$ cells subcutaneously in the neck area of wildtype and knockout mice. After subcutaneous injection of tumor cells or mock injection, mice were kept under standard conditions and had free access to food and water. After 21 days the animal were sacrificed, weighed and the tumor tissue was dissected. There was no significant difference in ATGL ko animals (Lipase A) between control (weight gain 1.84) and tumor bearing animals (weight gain 0.97) (FIG. 1A), demonstrating the cachexia is prevented in these ATGL ko animals. Tumor bearing HSL (Lipase B) ko animals did show a loss of body weight, but the loss was less pronounced than wild type animals (FIG. 1A). These changes cannot be attributed to differences in food intake (FIG. 1B).

Upon visual inspection, white adipose tissue (WAT) is completely lost 20 days after injection of tumor cells in wild type animals (FIG. 2A). WAT is preserved, however, in ATGL ko mice (FIG. 2B). This is also evident in the WAT weight (normalized to body weight) (FIG. 3A). Loss of HSL (Lipase B) partially protects against loss of WAT. This effect is even better demonstrated in nuclear magnetic resonance (NMR) measurements. Twenty-one days after injection of tumor cells or mock injections, mice were sacrificed and organs and WAT were dissected. WAT weight was determined and normalized to body weight (mg/g) (FIG. 3A). NMR analysis for the assessment of total body fat content was performed before injection and immediately before sacrificing the animals respectively. Using NMR analysis, fat content is recorded as percentage and total fat weight is calculated from the animals' weight. Change (in g) is reported compared to the initial values before injection (FIG. 3B). Average fat change by NMR was negative and significant in wildtype and HSL (Lipase B) ko mice, ie it was significantly reduced from before injection, while mock infected animals gained fat. Lipase A (ATGL) ko mice showed only a slight reduction versus mock infected mice, and a significant gain overall during the tumor experiment.

Further studies looked at lipase activity upon tumor-induced loss of adipose tissue. Animals were sacrificed 14 days after injection of tumor cells or mock injection, a time point where adipose tissue still can be dissected from wild type tumor bearing mice. Lipase activity was measured in homogenates of adipose tissue without (total lipase activity) or with inhibition of HSL by the HSL inhibitor 76-0079 (NNC 0076-0000-0079, provided by NovoNordisk, Denmark) (Lipase B inhibitor) (Schweiger M et al (2006) J Biol Chem 281(52): 40236-40241). Total lipase activity is increased approximately 3-fold in tumor bearing wild type animals (FIG. 4, WT, white bar) vs control wild type animals (FIG. 4, WT, black bar). This is in part due to an increase of ATGL activity as seen after inhibition of HSL (FIG. 4, WT+Lipase B inhibitor, black vs. white bar). ATGL tumor bearing mice show only a modest (40%) increase of total lipase activity (FIG. 4, lipase A ko, black vs. white bar). No lipase activity is seen (as expected) in ATGL ko also inhibited for HSL (FIG. 4, Lipase A ko+Lipase B inhibitor). Tumor bearing HSL ko animals show an over 2-fold induction of total lipase activity (FIG. 4, Lipase B ko), which is attributable to ATGL induction.

Changes in muscle mass were determined in mock infected and tumor bearing mice including wildtype, Lipase A (ATGL) ko mice, and Lipase B (HSL) ko mice. Twenty-one days after injection of tumor cells or mock injections, mice were sacrificed. *M. gastrocnenius* and *M. soleus* were dissected from both hind legs and the weight recorded. Muscle weight normalized to body weight is compared to the mock injected animals. In tumor-bearing animals, 50% of *M. gastrocnenius* (fast twitching skeletal muscle) muscle mass is lost in wild type animals and HSL ko animals (FIG. 5A, WT and Lipase B ko respectively). No loss of *M. gastrocnenius* muscle mass is seen in ATGL ko mice (FIG. 5A, Lipase A ko). No significant changes are seen in *M. soleus* (slow twitching skeletal muscle) mass in wildtype, Lipase A ko or Lipase B ko animals (FIG. 5B). These results confirm the inhibition of skeletal muscle loss in mice lacking ATGL.

Proteasome activity is a measure of intracellular and myofibrillar protein breakdown. Proteasome activity was measured in mock infected and tumor bearing mice including wildtype, Lipase A (ATGL) ko mice, and Lipase B (HSL) ko mice (FIG. 6A). Proteasome actiovity is two-fold higher in tumor bearing wild type mice compared to control (WT, highly significant) and a 25% increase is seen in HSL ko animals (Lipase B ko, significant). No proteasome activity increase is seen in ATGL (Lipase A) ko animals.

Caspase activity, an indicator of apoptotic cell death was measured in mock infected and tumor bearing mice including wildtype, Lipase A (ATGL) ko mice, and Lipase B (HSL) ko mice (FIG. 6B). An incremental increase in caspase activity is seen in tumor bearing wild type mice (FIG. 6B, wt_8, wt_14 and wt_21 days). No significant changes are recorded in ATGL (Lipase A) ko animals, wither at 14 or 21 days.

Materials and Methods

Lipase Assay (Triacylgycerol Hydrolase Assay):

Mesenteric, retroperitoneal, omental and, gonadal white adipose tissues (WAT) of wild-type (wt), Adipose Tri-Glyceride Lipase-knockout (ATGL-ko) and, Hormone Sensitive Lipase-knockout (HSL-ko) mice were removed surgically and, washed in phosphate-buffered saline (PBS) containing 1 mM ethylenediaminetetraacetic-acid (EDTA). The tissue was homogenized in lysis buffer (0.25 M sucrose, 1 mM EDTA, 1 mM dithiothreitol, 20 µg/ml leupeptin, 2 µg/ml antipain, 1 µg/ml pepstatin, pH 7.0) using a Magna Lyser (Roche diagnostics GmbH, Mannheim, Germany). The WAT lysate was centrifuged at 100,000 g for 1 hour (h) at 4° C. The lipid-free infranatant (cytosolic fraction) was collected and, used for triacyl-glycerol (TG) hydrolase assays. The substrate for the measurement of lipase activity containing triolein and [9, 10-3H(N)-triolein] (NEN Life Science Products, Boston, Mass.) as radioactive tracer was emulsified with phosphatidylcholine/phosphatidylinositol using a conventional ultrasound sonicator. The cytosolic fractions supplemented with or, without a specific inhibitor for HSL were incubated at 37° C. for 60 min under constant shaking. The reaction was terminated by addition of 3.25 ml methanol/chloroform/heptane (10:9:7) and, 1 ml of 0.1 M potassium carbonate and, 0.1 M boric acid (pH 10.5). After centrifugation at 800 g for 20 minutes (min) the radioactivity in 1 ml of the upper phase was determined by liquid scintillation counting in a LS 6500 Multi-Purpose Scintillation Counter from Beckman Coulter Inc. (Fullerton, Calif.).

Proteasome Assay:

*Musculus gastrocnemius* was homogenized in lysis buffer (20 mM Tris-HCl [pH 7.2], 0.1 mM EDTA, 1 mM 2-mercaptoethanol, 1 mM Dithiothreitol [DTT], 5 mM ATP, 20% glycerol, 0.04% (v/v) Triton X-100) using a magna lyser (Roche diagnostics GmbH, Mannheim, Germany) at 4° C. The lysate was centrifuged at 13,000 g for 15 mins at 4° C. The supernatant was collected and, protein concentration was determined with the RC DC Protein assay kit (BioRad, Hercules, Calif.). The chymotrypsin like proteasome activity was determined by incubating 40 µg protein with 0.167 µg/µl N-succinyl-Leu-Leu-Val-Try-7-amido-4-methylcoumarin (N-Suc LLVY-AMC, Sigma, St. Louis, Mo.) in incubation buffer (100 mM Tris-HCl [pH 7.4], 50 mM [HEPES pH 8.0] and 5 mmol/l Ethyleneglycoltetraacetic-acid[EGTA]) for 60 mins at 37° C. Fluorescence was read with a conventional spectrofluorometer at 380 nm excitation and, 460 nm emission. Adapted from (Busquets et al., 2004; Ventrucci et al., 2004)

Caspase Assay:

About 15 mg to 25 mg tissue from *Musculus gastrocnemius* was homogenized at 4° C. in 300 µl homogenisation buffer (25 mM HEPES pH 7.5; 5 mM MgCl$_2$; 1 mM EGTA; 1 mM Pefabloc SC; 1% Protease-Inhibitor-cocktail [v/v] [P8340 from Sigma, St. Louis, Mo.]. The lysate was centrifuged at 13,000 g for 20 min at 4° C. The supernatant was collected and the protein-content was measured using the DC Protein Assay from Bio-Rad, Hercules, Calif. Caspase activity was determined by incubating 50 μg protein (in 100 μl solution) with 100 μl of Caspase-Glo® 3/7 Reagent (Promega Corp., Madison, Wis.) for 1.5 hrs at 20° C. and, luminescence was measured using a luminometer (LUMIstar Optima BMG Labtec, Offenburg, GERMANY).

Animal Care:

Female C57BL/6J mice were maintained on a regular light-dark cycle (12 h light, 1.2 h dark) and, kept on a standard laboratory chow diet (4.5% w/w fat). HSL-ko and, ATGL-ko mice were generated by targeted homologous recombination, as described by (Haemmerle et al., 2006) (Haemmerle et al., 2002). Mice used for experiments were 8-9 weeks old. During the experiments, food intake (g) as well as mouse body weight (g) were measured daily using a conventional laboratory weighing balance.

Animal Treatment and Tissue Harvesting:

Mice were randomly divided into two groups: control non-tumour-bearing mice and, lewis lung carcinoma (LLC)-bearing mice. Mice were fasted for 12 h and subsequently anesthetized using isoflurane. Thereafter blood samples were collected by retro-orbital puncture from each mouse. Subsequently, $4 \times 10^6$ LLC-cells obtained from an exponentially proliferating cell-culture, maintained in conventional DMEM high glucose cell culture medium, containing 10% Fetal bovine serine [v/v], were subcutaneously injected at dorsum just below the neck. After different time periods (8 days, 14 days, 21 days) the mice were anaesthetized using isoflurane, blood samples were taken, as described above and, mice were kept in an unconscious state using 1% isoflurane. *Musculus. gastrocnemius* and, *Musculus soleus* were excised rapidly, and either frozen in liquid nitrogen, or stored in 4% neutral buffered formalin for subsequent preparation of paraffin blocks. Thereafter, mice were sacrificed by cervical dislocation, and tissues were rapidly excised, weighed, and either frozen in liquid nitrogen, or stored in formalin.

Blood and Plasma Parameters:

Serum levels of TG, glycerol, and FA were determined using commercial kits (Thermo Electron corp., Victoria, Australia; Sigma, St. Louis, Mo.; Wako Chemicals, Neuss, Germany). Blood glucose concentration was determined using Accu-Check glucometer (Roche Diagnostics, Vienna, Austria).

NMR

The mice were anesthetized using isofurane, and whole body fat mass was measured using the Minispec mq NMR analyzer (Brucker Optics, Woodlands, Tex.) as described by (Tinsley et al., 2004).

H&E

Paraffin-embedded, formalin-fixed specimen cross-sections were stained by hematoxylin, and counter-stained by eosin using standard methods.

Example 2

Screening

The activity of ATGL can primarily be measured by cleavage of triglycerides (exemplary assay provided in Example 1 above Lipase Assay), because the enzyme does not recognize water-soluble substrates. Using this method, about 300 measurements can be carried out per day by one person in a throughput assay.

ATGL activity may also be measured using cell culture. Preadipocyte-lines, e.g. 3T3-L1 cells, are differentiated to adipocytes. Then after beta-adrenergic stimulation, these cells secrete large amounts of glycerol and fatty acids into the culture medium, which can be measured easily using commercial enzymatic kits. By incubation with inhibitors, this secretion can be inhibited. In the absence of ATGL, the secretion is inhibited by about 70%. In the absence of HSL and ATGL, there is almost no beta-adrenergic stimulation of lipolysis in adipocytes (Schweiger M et al (2006) J Biol Chem 281(52):40236-40241). Therefore, in the presence of an HSL inhibitor (such as 76-0079, Novo Nordisk), specific ATGL activity can be determined in living adipocytes (Schweiger M et al (2006) J Biol Chem 281(52):40236-40241).

ATGL inhibition activity of a phospholipase-inhibitor (R)-Bromoenol lactone (Cayman Chemicals, Cat. No. 10006800, CAS No. 478288-90-3) has been demonstrated with expressed ATGL (Jenkins C M et al (2004) J Biol Chem 279(47):48968-48975) or native ATGL in hepatocytes (Chung C et al (2008) J Hepatol 48:47$_{1-4}$78). This lipase inhibitor also inhibits other lipases including iPLA$_2$β and iPLA$_2$γ (Mancuso D J et al (2000) J boil Chem 275:9937-9945; Hazen S et al (1991) J Biol Chem 266:7227-7232; Zupan L A et al (1993) J med Chem 36:95-100). This provides an ATGL inhibiting compound for studies, assessment, and as a control in further screening.

To further assess ATGL hydrolysis of neutral lipids, His-tagged ATGL can be transiently expressed in COS-7 cells using a eukaryotic expression vector. For comparison, COS-7 cells are also transfected with a similar construction expressing His-tagged HSL. Extracts from transfected cells are pre-incubated with an inhibitor or candidate compound or compound library. When extracts are preincubated with the fluorescent lipase inhibitor (NBD-HEHP) and subsequently subjected to SDS-PAGE analysis and fluorography, fluorescent signals can be observed in positions corresponding to the expected molecular weight of ATGL and HSL providing evidence that ATGL is enzymatically active in transfected COS cells. To confirm ATGL activity, TG-hydrolase activity assays can be performed using a radioactively labelled [9, 10-3H (N))]-triolein substrate. AS controls, no enzymatic activities should be observed when radioactively labeled retinyl palmitate, cholesteryl oleate or phosphatidylcholine are used as lipid substrates.

To determine ATGL function in adipocytes, including in assays in the presence or absence of one or more candidate compounds, modulators, or inhibitors, a recombinant adenovirus encoding His-tagged full length mouse or human ATGL cDNA is constructed and used to infect mouse 3T3-L1 adipocytes at day 6 of differentiation. Western blotting analysis of cell-extracts of infected adipocytes reveals expression of His-tagged. ATGL at the appropriate molecular weight. Overexpression of ATGL in adipocytes can markedly augment both basal and isoproterenol-stimulated lipolysis, indicative of a functional ATGL lipase in adipose tissue.

Material and Methods cDNA Cloning and Transient Expression of Recombinant His-Tagged Proteins in COS-7 Cells and 3T3-L1 Adipocytes.

The coding sequences of mouse ATGL and HSL are amplified by PCR from cDNA prepared from mRNA of mouse white adipose tissue by reverse transcription. The open reading frame, flanked by KpnI/XhoI sites for ATGL and HSL were cloned into the eucaryotic expression vector pcDNA4/HisMax (Invitrogen). Transfection of COS-7 cells was performed with Metafectene™ (Biontex) according to the manufacturer's description. The PCR primers used to generate these probes were as follows.

ATGL forward 5'-<u>TGGTACCG</u>TTCCCGAGGG AGAC-CAAGTGGA-3' (SEQ ID NO. 5),

ATGL revers 5'-<u>CCTCGAGC</u>GCAAGGCGGG AGGC-CAGGT-3' (SEQ ID NO. 6),

HSL forward 5'-<u>TGGTACCT</u>-ATGGATTTACG CAGAT-GACACA-3' (SEQ ID NO. 7),

HSL revers 5'-<u>CCTCGAGC</u>GTTCAGTGGTGCA GCAGGCG-3' (SEQ ID NO. 8).

```
ATGL forward
5'-TGGTACCGTTCCCGAGGGAGACCAAGTGGA-3',

ATGL revers
5'-CCTCGAGCGCAAGGCGGGAGGCCAGGT-3'.

HSL forward
5'-TGGTACCT-ATGGATTTACGCACGATGACACA-3',

HSL revers
5'-CCTCGAGCGTTCAGTGGTGCAGCAGGCG-3'.
```

Construction of the Recombinant Adenovirus for ATGL Expression (ATGL-Ad) and Infection of 3T3-L1 Cells:

The recombinant adenovirus coding for mouse ATGL is prepared by cotransfection of the shuttle plasmid pAvCvSv containing the ATGL cDNA and pJM 17 into HEK-293 cells. The 1.65 kb Mlu I-Cla I flanked mouse ATGL cDNA fragment (His-tag included) is amplified by PCR from the eucaryotic expression vector pcDNA4/HisMax containing mouse ATGL cDNA and subcloned into Mlu I-Cla I digested pAvCvSv. The resulting shuttle plasmid is cotransfected with pJM 17 into HEK-293 cells using the calcium phosphate coprecipitation method. Large scale production of high titer recombinant ATGL-Ad is performed as described elsewhere. 3T3-L1 fibroblasts were cultured in DMEM containing 10% FCS and differentiated using a standard protocol (Bernlohr, D. A. et al (1985) Biol Chem 260: 5563-7). Adipocytes are infected on day 8 of differentiation with a multiplicity of infection (moi) of ~400 plaque forming units/cell. For that purpose appropriate pfu are preactivated in DMEM containing 0.5 µg/ml of polylysin for 100 min and afterwards the cells are incubated with this virus suspension for 24 hours. After 24 h the medium is removed and the cells are incubated for further 24 h with complete medium. For most of the experiments, recombinant adenovirus expressing β-galactosidase was used as a control (LacZ-Ad).

Western Analysis.

Cellular proteins are separated by SDS-polyacrylamide gel electrophoresis and transferred to a nitrocellulose membrane (Schleicher & Schuell, Germany). For detection of His-tagged proteins, blots were incubated with 1/10000 diluted Anti-His monoclonal antibody (6xHis, Cionetech). Perilipin is detected using a guinea pig polyclonal antibody against Perilipin A and B (PROGEN). Bound immunoglobulins are detected with a HRP-labeled IgG conjugates (Vector Inc.) and visualized by ECL detection (ECL plus, Amersham Pharmacia Biotech, Germany) on a Storm Image Analysis system. Quantitation is performed using ImageQuant Software.

Reaction of ATGL and HSL with the Fluorescent Lipase Inhibitor NBD-HEHP.

Transfected COS-7 cells are washed twice with PBS, scraped into lysis buffer (0.25 M sucrose, 1 mM EDTA, 1 mM dithioerythritol, 20 µg/ml leupeptin, 2 µg/ml antipain, 1 µg/ml pepstatin) and disrupted on ice by sonication. Nuclei and unbroken materials are removed by centrifugation at 1.000 g at 4° C. for 15 min to obtain cytoplasmatic extracts. 50 µg of protein is incubated with 1 nmol fluorescently labelled lipase inhibitor O-((6-(7-Nitrobenz-2-oxa-1,3-diazol-4-yl)amino) hexanoyl)aminoethyl-O-(n-hexyl)phosphonic acid p-nitrophenyl ester (NBD-HEHP) (Oskolkova, O. V. et al (2003) Chem Phys Lipids 125:103-14) and 1 mM Triton X-100 (especially purified for membrane research, Hofmann LaRoche) at 37° C. for 2 hours under shaking. Protein is precipitated with 10% TCA for 1 h on ice, washed with acetone and separated by 10% SDS-PAGE. Gels are fixed in 10% ethanol and 7% acetic acid. Fluorescence is detected with a BioRad FX Pro Laserscanner (excitation 488 nm, emission 530 nm).

Northern Analysis.

The cDNA probe for northern blot analysis of mouse ATGL is prepared by RT-PCR by use of first-strand cDNA from mouse fat mRNA. PCR primers used to generate this probe are as follows: forward 5'-TGGAACATCTCAT-TCGCTGG-3' (SEQ ID NO. 9), reverse 5'-AATGCCGC-CATCCACATAG-3' (SEQ ID NO. 10). Total RNA was isolated from various mouse tissues using the TRI Reagent procedure according to manufacturer's protocol (Molecular Research Center, Karlsruhe, Germany). Specific mRNAs were detected using standard Northern blotting techniques with 10 µg total RNA. $^{32}$P-labeled probes for hybridization were generated using random priming. Northern blots are visualized by exposure to a PhosphorImager Screen (Apbiotech, Freiburg, Germany) and analyzed using ImageQuant Software.

Assay for TG Lipase, Cholesteryl Esterase, Retinyl Esterase and Phospholipase Activity.

For determination of lipase activity 0.1 ml of cytosolic extracts and 0.1 ml substrate are incubated in a water bath at 37° C. for 60 min. The reaction is terminated by adding 3.25 ml of methanol/chloroform/heptane (10:9:7) and 1 ml of 0.1 M potassium carbonate, 0.1 M boric acid, pH 10.5. After centrifugation (800 g, 20 min) the radioactivity in 1 ml of the upper phase is determined by liquid scintillation counting. Neutral lipase activity is measured in 50 mM potassium phosphate buffer, pH 7.0 and 2.5% defatted BSA. The substrate for neutral TG lipase activity contained 33 nmol triolein/assay with [9,10-$^3$H(N)]-triolein (40.000 cpm/nmol, NEN Life Science Products) as radioactive tracer for COS-7 cells and 167 nmol/assay for 3T3-L1 adipocytes (7300 cpm/nmol). The substrates for cholesteryl esterase and retinyl esterase activity contained 10 nmol/assay of cholesteryl oleate or retinyl palmitate and the corresponding tracers cholesteryl [9,10-$^3$H]-oleate or retinyl [9,10-$^3$H(N)]-palmitate (50.000 cpm/nmol). For determination of phospholipase activity in cytosolic extracts the substrate contained 20 nmol/assay phosphatidylcholine and [dipalmitoyl-1-$^{14}$C]-phosphatidylcholine (12.000 cpm/nmol). All substrates are prepared by sonication (Virsonic 475) essentially as described (30).

Determination of FA and Glycerol Release from 3T3-L1 Adipocytes.

Cells are incubated in DMEM medium (GIBCO) containing 2% fatty acid free BSA (Sigma) with or without 10 µM isoproterenol (Sigma) at 37° C. Aliquots of the medium were collected and investigated for the FFA and glycerol content by using commercial kits (WAKO).

Animal Models of Cachexia

Lewis lung carcinoma cells are used in mice to generate tumors and cachexia effects as described above herein. Lewis lung carcinoma cells were obtained from the European Collection of Cell Cultures (ECACC) and maintained in cell culture before injecting ~4×10$^6$ cells subcutaneously in the neck area of mice. Lewis lung carcinoma is a cell line established from the lung of a C57BL mouse bearing a tumor resulting from an implantation of primary Lewis lung carcinoma. The cells are reported to be highly tumorigenic, but weakly metastatic in mice (Laster, W. R. et al (1971) Proc of the Amer Assoc for Cancer Research 12(NMAR):7).

REFERENCES

Busquets, S., Figueras, M. T., Fuster, G., Almendro, V., Moore-Carrasco, R., Ametller, E., Argiles, J. M., and Lopez-Soriano, F. J. (2004). Anticachectic effects of formoterol: a drug for potential treatment of muscle wasting. Cancer Res 64, 6725-6731.

Haemmerle, G., Lass, A., Zimmermann, R., Gorkiewicz, G., Meyer, C., Roman, J., Heldmaier, G., Maier, R., Theussl, C., Eder, S., et al. (2006). Defective lipolysis and altered energy metabolism in mice lacking adipose triglyceride lipase. Science 312, 734-737.

Haemmerle, G., Zimmermann, R., Hayn, M., Theussl, C., Waeg, G., Wagner, E., Sattler, W., Magin, T. M., Wagner, E. F., and Zechner, R. (2002). Hormone-sensitive lipase deficiency in mice causes diglyceride accumulation in adipose tissue, muscle, and testis. J Biol Chem 277, 4806-4815.

Tinsley, F. C., Taicher, G. Z., and Heiman, M. L. (2004). Evaluation of a quantitative magnetic resonance method for mouse whole body composition analysis. Obes Res 12, 150-160.

Ventrucci, G., Mello, M. A., and Gomes-Marcondes, M. C. (2004). Proteasome activity is altered in skeletal muscle tissue of tumour-bearing rats a leucine-rich diet. Endocr Relat Cancer 11, 887-895.

Example 3

ATGL Inhibitors

Figure 9:
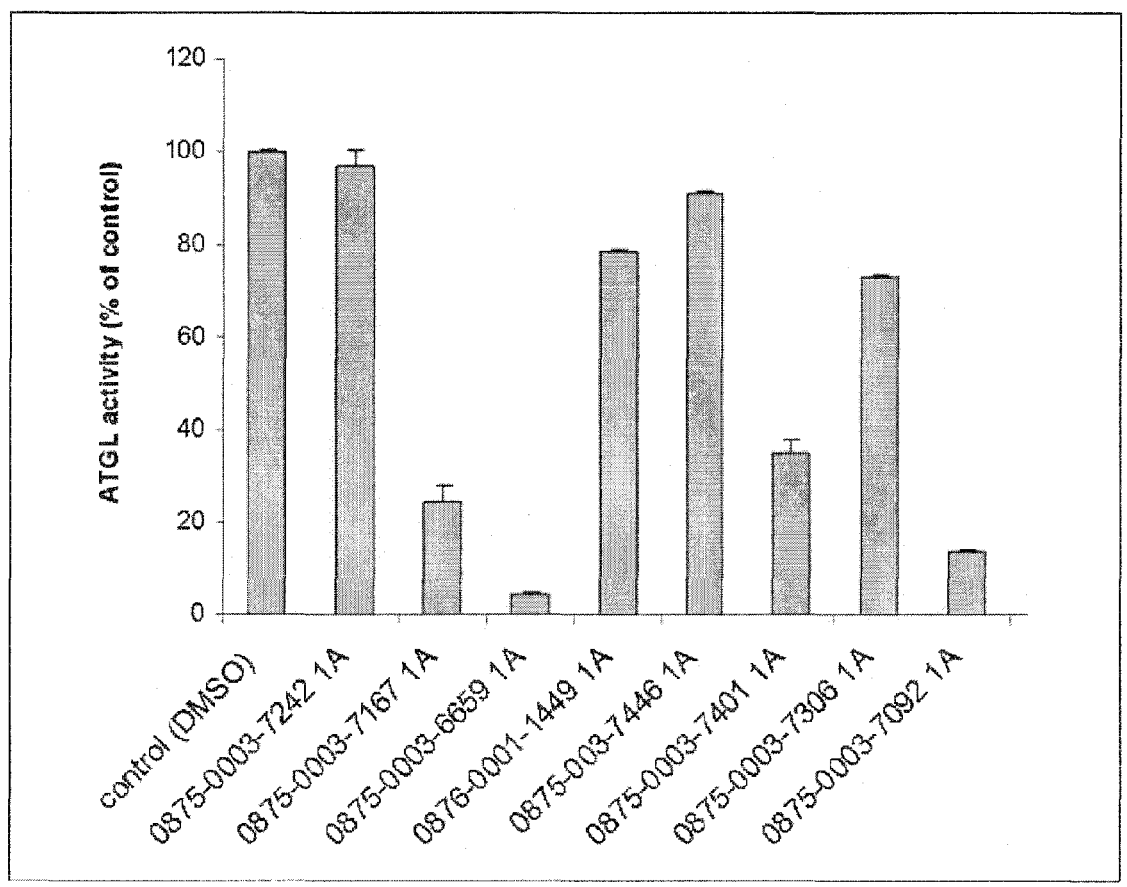
FIG. 9 depicts results of assay of ATGL activity (% control) in the presence of control (DMSO) and candidate inhibitors. The compounds are delineated Compound 1 (control DMSO) Compound 2 (0875-0003-7242), Compound 3 (0875-0003-7167), Compound 4 (0875-0003-6659), Compound 5 (0876-0001-1449), Compound 6 (0875-0003-7446), Compound 7 (0875-0003-7401), Compound 8 (0875-0003-7306), and Compound 9 (0875-0003-7092).

A Lipase assay (triglyceride hydrolase assay) as described above was performed with candidate inihitors. The structures are depicted further below. FIG. 9 shows that some of the candidate inhibitor substances inhibit ATGL. The inhibitor with the largest degree of inhibition in this assay is 6659 (No. 4, CHEMDIV (3254-0350). Compounds No. 3 (7167), 7 (7401), and 9 (7092) also inhibit ATGL.

These active compounds were initially identified upon screening for HSL inhibitors. First, lipolysis was tested in cell culture assay with cultivated adipocytes. The substances were then tested for inhibiton of HSL in vitro. Some of the substances inhibited lipolysis in cell culture, but had no effect on HSL in the in vitro assay. These substances were checked for inhibitory activity against ATGL.

Compound 9

0875-0003-7092
CHEMDIV (4112-0423)

Compound 8

0875-0003-7306
CHEMDIV (4275-2216)

Compound 7

0875-0003-7401
CHEMDIV (4356-2701)

Compound 6

0875-0003-7446
CHEMDIV (4427-1195)

Compound 5

0876-0001-1449
ASINEX (AEM 11160086)

Compound 4

0875-0003-6659
CHEMDIV (3254-0350)

Compound 3

0875-0003-7167
CHEMDIV (8012-8567)

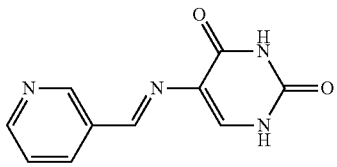

0875-0003-7242
CHEMDIV (4209-0100)

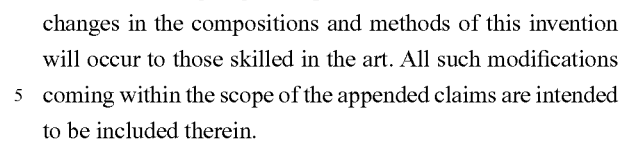

Compound 2

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

We claim:

1. A method for treatment of cachexia in a subject comprising administering to said subject a therapeutically effective amount of an agent that inhibits the expression or activity of adipose triglyceride lipase (ATGL), wherein the agent is a compound prepared by a method comprising the steps:
   a) contacting one or more compounds suspected of having ATGL inhibitory activity with a cell expressing ATGL polypeptide; and
   b) measuring the expression and/or activity of ATGL in the presence or absence of said compound,
wherein a compound that blocks or reduces the expression and/or activity of ATGL is identified as a compound that inhibits cachexia.

2. A method for treatment of cachexia in a subject comprising administering to said subject a therapeutically effective amount of agent that inhibits the expression or activity of adipose triglyceride lipase (ATGL), wherein the agent is a compound prepared by a method comprising the steps:
   (a) contacting a compound with an ATGL polypeptide comprising an amino acid sequence selected from the group consisting of SEQ ID NO:1 AND SEQ ID NO:3 which is present in an in vitro cell-free preparation or in a mammalian cell;
   (b) determining the ability of the compound to inhibit the expression or activity of said ATGL polypeptide by measuring the enzymatic activity, the expression of said polypeptide, and/or, if said polypeptide is in an in vitro cell-free preparation, the binding affinity of said compound to said polypeptide; and wherein said property is the enzymatic activity of said polypeptide, the expression of said polypeptide, and/or, if said polypeptide is in an in vitro cell free preparation, the binding affinity of said compound to said polypeptide (c) selecting a compound that inhibits the expression or activity of said ATGL polypeptide.

3. The method of claim 2, further defined as comprising the steps of:
   (i) contacting a population of mammalian cells expressing said ATGL polypeptide with the compound that exhibits a binding affinity of at least 10 micromolar; and
   (ii) identifying a compound that inhibits hydrolysis of triglyceride by ATGL.

4. A method for treatment of cachexia in a subject comprising administering to said subject a therapeutically effective amount of agent that inhibits the expression or activity of adipose triglyceride lipase (ATGL), wherein the agent is a compound, prepared by a method comprising the steps of:
   (a) contacting a population of mammalian cells expressing said polypeptide with the compound that significantly inhibits the expression or activity of the polypeptide; and
   (b) identifying the compound that inhibits cachexia.

5. The method according to claim 1, which additionally comprises the step of comparing the compound to be tested to a control.

6. The method according to claim 1, wherein the compound is further contacted with a cell expressing hormone-sensitive lipase (HSL) and at least one other lipase polypeptide, and measuring the expression or activity of the HSL and the at least one other lipase polypeptide.

7. A method for treatment of cachexia in a subject comprising administering to said subject a therapeutically effective amount of agent that inhibits the expression or activity of adipose triglyceride lipase (ATGL), wherein the agent is a compound of a formula selected from the group consisting of (i) compound of formula (I)

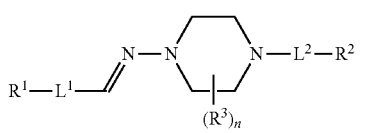

wherein:
- $L^1$ is a bond, $C_{1-10}$ alkylene, $C_{2-10}$ alkenylene, or $C_{2-10}$ alkynylene, wherein said alkylene, said alkenylene or said alkynylene is optionally substituted with one or more groups independently selected from halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), and further wherein one or more —$CH_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —$SO_2$—;
- $L^2$ is a bond, $C_{1-10}$ alkylene, $C_{2-10}$ alkenylene, or $C_{2-10}$ alkynylene, wherein said alkylene, said alkenylene or said alkynylene is optionally substituted with one or more groups independently selected from halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), and further wherein one or more —$CH_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —$SO_2$—;
- $R^1$ is optionally substituted aryl or optionally substituted heteroaryl, wherein said aryl or said heteroaryl may be substituted with one or more groups independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);
- $R^2$ is optionally substituted aryl or optionally substituted heteroaryl, wherein said aryl or said heteroaryl may be substituted with one or more groups independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);
- n is an integer of 0 to 8; and
- each $R^3$ is independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);
- or a pharmaceutically acceptable salt, solvate or prodrug thereof, (ii) formula (II)

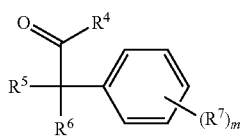

wherein:
- $R^4$ is selected from —OH, —O($C_{1-4}$ alkyl), —$NH_2$, —NH($C_{1-4}$ alkyl), —N($C_{1-4}$ alkyl)($C_{1-4}$ alkyl), —SH, or —S($C_{1-4}$ alkyl);
- $R^5$ is selected from —OH or —O($C_{1-4}$ alkyl);
- $R^6$ is —$CF_3$ or CN;
- m is an integer of 0 to 5; and
- each $R^7$ is independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);
- or a pharmaceutically acceptable salt, solvate or prodrug thereof;

(iii) formula (III)

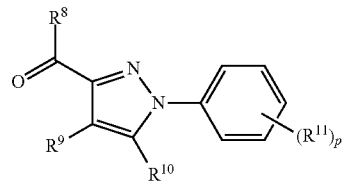

wherein:
- $R^8$ is selected from —OH, —O($C_{1-4}$ alkyl), —$NH_2$, —NH($C_{1-4}$ alkyl), —N($C_{1-4}$ alkyl)($C_{1-4}$ alkyl), —SH, or —S($C_{1-4}$ alkyl);
- $R^9$ is selected from $C_{1-4}$ alkyl, halogen, —CN, —OH, —O($C_{1-4}$ alkyl), —$NH_2$, —NH($C_{1-4}$ alkyl), or —N($C_{1-4}$ alkyl)($C_{1-4}$ alkyl);
- $R^{10}$ is selected from $C_{1-4}$ alkyl, halogen, —CN, —OH, —O($C_{1-4}$ alkyl), —$NH_2$, —NH($C_{1-4}$ alkyl), or —N($C_{1-4}$ alkyl)($C_{1-4}$ alkyl) or hydrogen
- p is an integer of 0 to 5; and
- each $R^{11}$ is independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);
- or a pharmaceutically acceptable salt, solvate or prodrug thereof, or (iv) formula (IV)

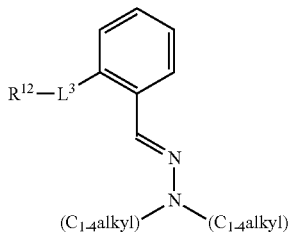

wherein:
- $L^3$ is a bond, $C_{1-10}$ alkylene, $C_{2-10}$ alkenylene, or $C_{2-10}$ alkynylene, wherein said alkylene, said alkenylene or said alkynylene is optionally substituted with one or more groups independently selected from halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl), and further wherein one or more —$CH_2$— units comprised in said alkylene, said alkenylene or said alkynylene are each optionally replaced by a group independently selected from —O—, —NH—, —N($C_{1-4}$ alkyl)-, —CO—, —CO—NH—, —NH—CO—, —S—, —SO—, or —$SO_2$—; and R[12] is optionally substituted aryl or optionally substituted heteroaryl, wherein said aryl or said heteroaryl may be substituted with one or more groups independently selected from $C_{1-4}$ alkyl, halogen, —$CF_3$, —CN, —OH, —O($C_{1-4}$ alkyl), —$NH_2$, —NH($C_{1-4}$ alkyl), or —N($C_{1-4}$ alkyl)($C_{1-4}$ alkyl);

or a pharmaceutically acceptable salt, solvate or prodrug thereof.

8. The method of claim 7, wherein said compound is a compound having the formula selected from the group consisting of:

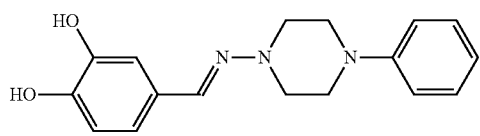

(i)

or a pharmaceutically acceptable salt, solvate or prodrug thereof

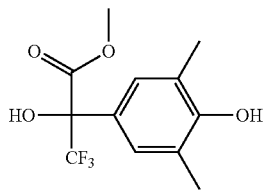

(ii)

or a pharmaceutically acceptable salt, solvate or prodrug thereof;

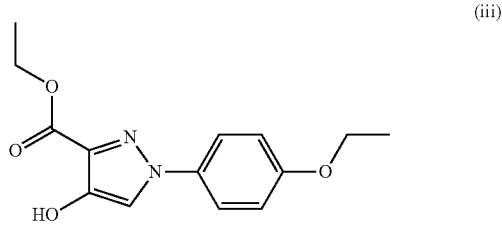 [SMILES: CCOC(=O)c1nn(-c2ccc(OCC)cc2)cc1O]

(iii)

or a pharmaceutically acceptable salt, solvate or prodrug thereof, and

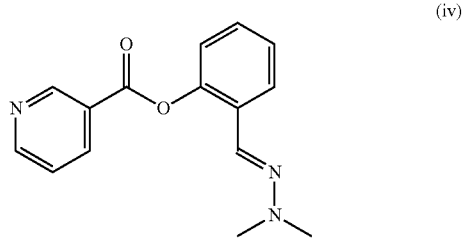 [SMILES: CN(C)/N=C/c1ccccc1OC(=O)c1cccnc1]

(iv)

or a pharmaceutically acceptable salt, solvate or prodrug thereof.

9. A method for treatment of cachexia in a subject comprising administering to said subject a therapeutically effective amount of agent that inhibits the expression or activity of adipose triglyceride lipase (ATGL), wherein the agent is a compound selected from the group consisting of Compound 3 (CHEMDIV (8012-8567)), Compound 4 (CHEMDIV (3254-0350)), Compound 7 (CHEMDIV (4356-2701)), Compound 9 (CHEMDIV (4112-0423)).

* * * * *

UNITED STATES PATENT AND TRADEMARK OFFICE
CERTIFICATE OF CORRECTION

| | |
|---|---|
| PATENT NO. | : 8,993,509 B2 |
| APPLICATION NO. | : 13/262094 |
| DATED | : March 31, 2015 |
| INVENTOR(S) | : Robert Zimmerman et al. |

Page 1 of 1

It is certified that error appears in the above-identified patent and that said Letters Patent is hereby corrected as shown below:

On title page, item (60) Related U.S. Application Data, delete "Mar. 31, 2010" and insert --Mar. 31, 2009--.

In the Claims:

In claim 2, column 61, lines 63-67, delete "wherein said property is the enzymatic activity of said polypeptide, the expression of said polypeptide, and/or, if said, polypeptide is in an in vitro cell free preparation, the binding affinity of said compound to said polypeptide".

Signed and Sealed this
Fifteenth Day of September, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 504
<212> TYPE: PRT
<213> ORGANISM: Homo Sapiens

<400> SEQUENCE: 1

```
Met Phe Pro Arg Glu Lys Thr Trp Asn Ile Ser Phe Ala Gly Cys Gly
1               5                   10                  15

Phe Leu Gly Val Tyr Tyr Val Gly Val Ala Ser Cys Leu Arg Glu His
                20                  25                  30

Ala Pro Phe Leu Val Ala Asn Ala Thr His Ile Tyr Gly Ala Ser Ala
            35                  40                  45

Gly Ala Leu Thr Ala Thr Ala Leu Val Thr Gly Val Cys Leu Gly Glu
        50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
                85                  90                  95

Phe Leu Leu Lys Val Leu Pro Ala Asp Ser His Glu His Ala Ser Gly
                100                 105                 110

Arg Leu Gly Ile Ser Leu Thr Arg Val Ser Asp Gly Glu Asn Val Ile
            115                 120                 125

Ile Ser His Phe Asn Ser Lys Asp Glu Leu Ile Gln Ala Asn Val Cys
    130                 135                 140

Ser Gly Phe Ile Pro Val Tyr Cys Gly Leu Ile Pro Pro Ser Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
                180                 185                 190

Ile Cys Pro Gln Asp Ser Ser Thr Asn Ile His Glu Leu Arg Val Thr
            195                 200                 205

Asn Thr Ser Ile Gln Phe Asn Leu Arg Asn Leu Tyr Arg Leu Ser Lys
    210                 215                 220

Ala Leu Phe Pro Pro Glu Pro Leu Val Leu Arg Glu Met Cys Lys Gln
225                 230                 235                 240

Gly Tyr Arg Asp Gly Leu Arg Phe Leu Gln Arg Asn Gly Leu Leu Asn
                245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
```

|  |  |  |  |  | 275 |  |  |  |  | 280 |  |  |  |  | 285 |  |
|---|---|---|---|---|---|---|---|---|---|---|---|---|---|---|---|---|

Gln Leu Pro Gly Glu Asp His Ile Leu Glu His Leu Pro Ala Arg Leu
    290                      295                          300

Asn Glu Ala Leu Leu Glu Ala Cys Val Glu Pro Thr Asp Leu Leu Thr
305                      310                      315                  320

Thr Leu Ser Asn Met Leu Pro Val Arg Leu Ala Thr Ala Met Met Val
                325                      330                      335

Pro Tyr Thr Leu Pro Leu Glu Ser Ala Leu Ser Phe Thr Ile Arg Leu
            340                      345                      350

Leu Glu Trp Leu Pro Asp Val Pro Glu Asp Ile Arg Trp Met Lys Glu
            355                      360                      365

Gln Thr Gly Ser Ile Cys Gln Tyr Leu Val Met Arg Ala Lys Arg Lys
    370                      375                      380

Leu Gly Arg His Leu Pro Ser Arg Leu Pro Glu Gln Val Glu Leu Arg
385                      390                      395                  400

Arg Val Gln Ser Leu Pro Ser Val Pro Leu Ser Cys Ala Ala Tyr Arg
                405                      410                      415

Glu Ala Leu Pro Gly Trp Met Arg Asn Asn Leu Ser Leu Gly Asp Ala
            420                      425                      430

Leu Ala Lys Trp Glu Glu Cys Gln Arg Gln Leu Leu Leu Gly Leu Phe
    435                      440                      445

Cys Thr Asn Val Ala Phe Pro Pro Glu Ala Leu Arg Met Arg Ala Pro
450                      455                      460

Ala Asp Pro Ala Pro Ala Pro Asp Pro Ala Ser Pro Gln His Gln
465                      470                      475                  480

Leu Ala Gly Pro Ala Pro Leu Leu Ser Thr Pro Ala Pro Glu Ala Arg
            485                      490                      495

Pro Val Ile Gly Ala Leu Gly Leu
            500

```
<210> SEQ ID NO 2
<211> LENGTH: 2113
<212> TYPE: DNA
<213> ORGANISM: Homo sapiens

<400> SEQUENCE: 2
gcggccccag tcagacgcag gcagcccaa  agcctgaaca  ggcagggcca  gacccagctt      60
cttcgcctcc gccagcgggg accccgagct agagccgcag cgggacctgc ccggcccccg     120
gctccagcga gcgagcggcg agcaggcggc tcacagaggc ctggccgccc acggaacccg     180
gggcccggcg gccgccgccg cgatgtttcc ccgcgagaag acgtggaaca tctcgttcgc     240
gggctgcggc ttcctcggcg tctactacgt cggcgtggcc tcctgcctcc gcgagcacgc     300
gcccttcctg gtgccaacg ccacgcacat ctacggcgcc tcggccgggg cgctcacggc     360
cacggcgctg gtcaccgggg tctgcctggg tgaggctggt gccaagttca ttgaggtatc     420
taaagaggcc cggaagcggt tcctgggccc cctgcacccc tccttcaacc tggtaaagat     480
catccgcagt ttcctgctga aggtcctgcc tgctgatagc catgagcatg ccagtgggcg     540
cctgggcatc tccctgaccc gcgtgtcaga cggcgagaat gtcattatat cccacttcaa     600
ctccaaggac gagctcatcc aggccaatgt ctgcagcggt ttcatccccg tgtactgtgg     660
gctcatccct ccctccctcc agggggtgcg ctacgtggat ggtggcattt cagacaacct     720
gccactctat gagcttaaga acaccatcac agtgtccccc ttctcgggcg agagtgacat     780
ctgtccgcag gacagctcca ccaacatcca cgagctgcgg gtcaccaaca ccagcatcca     840
```

```
gttcaacctg cgcaacctct accgcctctc caaggccctc ttcccgccgg agccctggt      900
gctgcgagag atgtgcaagc agggataccg ggatggcctg cgctttctgc agcggaacgg      960
cctcctgaac cggcccaacc ccttgctggc gttgccccc  gcccgccccc acggcccaga     1020
ggacaaggac caggcagtgg agagcgccca gcggaggat  tactcgcagc tgccgggaga     1080
agatcacatc ctggagcacc tgcccgcccg gctcaatgag gccctgctgg aggcctgcgt     1140
ggagcccacg gacctgctga ccaccctctc caacatgctg cctgtgcgtc tggccacggc     1200
catgatggtg ccctacacgc tgccgctgga gagcgctctg tccttcacca tccgcttgct     1260
ggagtggctg cccgacgttc ccgaggacat ccggtggatg aaggagcaga cgggcagcat     1320
ctgccagtac ctggtgatgc gcgccaagag gaagctgggc aggcacctgc cctccaggct     1380
gccggagcag gtggagctgc cccgcgtcca gtcgctgccg tccgtgccgc tgtcctgcgc     1440
cgcctacaga gaggcactgc ccggctggat gcgcaacaac ctctcgctgg ggacgcgct      1500
ggccaagtgg gaggagtgcc agcgccagct gctgctcggc ctcttctgca caacgtggc      1560
cttcccgccc gaagctctgc gcatgcgcgc acccgccgac ccggctcccg cccccgcgga     1620
cccagcatcc ccgcagcacc agctggccgg gcctgccccc ttgctgagca ccctgctcc      1680
cgaggcccgg cccgtgatcg gggccctggg gctgtgagac cccgaccctc tcgaggaacc     1740
ctgcctgaga cgcctccatt accactcgcg agtgagatga ggggactcac agttgccaag     1800
aggggtcttt gccgtgggcc ccctcgccag ccactcacca gctgcatgca ctgagagggg     1860
aggtttccac accctcccc  tgggccgctg aggccccgcg cacctgtgcc ttaatcttcc     1920
ctcccctgtg ctgcccgagc acctcccccg cccctttact cctgagaact tgcagctgc      1980
ccttccctcc ccgttttca  tggcctgctg aaatatgtgt gtgaagaatt atttattttc     2040
gccaaagcac atgtaataaa tgctgcagcc caaaaaaaaa aaaaaaaaaa aaaaaaaaaa     2100
aaaaaaaaaa aaa                                                       2113

<210> SEQ ID NO 3
<211> LENGTH: 430
<212> TYPE: PRT
<213> ORGANISM: Mus musculus

<400> SEQUENCE: 3

Met Phe Thr Arg Glu Thr Lys Trp Asn Ile Ser Phe Ala Gly Cys Gly
1               5                   10                  15

Phe Leu Gly Val Tyr His Ile Gly Val Ala Ser Cys Leu Arg Glu His
                20                  25                  30

Ala Pro Phe Leu Val Ala Asn Ala Thr His Ile Tyr Gly Ala Ser Ala
            35                  40                  45

Gly Ala Leu Thr Ala Thr Ala Leu Val Thr Gly Ala Cys Leu Gly Glu
        50                  55                  60

Ala Gly Ala Asn Ile Ile Glu Val Ser Lys Glu Ala Arg Lys Arg Phe
65                  70                  75                  80

Leu Gly Pro Leu His Pro Ser Phe Asn Leu Val Lys Thr Ile Arg Gly
                85                  90                  95

Cys Leu Leu Lys Thr Leu Pro Ala Asp Cys His Glu Arg Ala Asn Gly
            100                 105                 110

Arg Leu Gly Ile Ser Leu Thr Arg Val Ser Asp Gly Glu Asn Val Ile
        115                 120                 125

Ile Ser His Phe Ser Ser Lys Asp Glu Leu Ile Gln Ala Asn Val Cys
    130                 135                 140
```

Ser Thr Phe Ile Pro Val Tyr Cys Gly Leu Ile Pro Pro Thr Leu Gln
145                 150                 155                 160

Gly Val Arg Tyr Val Asp Gly Gly Ile Ser Asp Asn Leu Pro Leu Tyr
            165                 170                 175

Glu Leu Lys Asn Thr Ile Thr Val Ser Pro Phe Ser Gly Glu Ser Asp
        180                 185                 190

Ile Cys Pro Gln Asp Ser Ser Thr Asn Ile His Glu Leu Arg Val Thr
    195                 200                 205

Asn Thr Ser Ile Gln Phe Asn Leu Arg Asn Leu Tyr Arg Leu Ser Lys
210                 215                 220

Ala Leu Phe Pro Pro Glu Pro Met Val Leu Arg Glu Met Cys Lys Gln
225                 230                 235                 240

Gly Tyr Arg Asp Gly Leu Arg Phe Leu Arg Arg Asn Ala Leu Leu Glu
            245                 250                 255

Ala Cys Val Glu Pro Lys Asp Leu Met Thr Thr Leu Ser Asn Met Leu
        260                 265                 270

Pro Val Arg Leu Ala Thr Ala Met Met Val Pro Tyr Thr Leu Pro Leu
    275                 280                 285

Glu Ser Ala Val Ser Phe Thr Ile Arg Leu Leu Glu Trp Leu Pro Asp
290                 295                 300

Val Pro Glu Asp Ile Arg Trp Met Lys Glu Gln Thr Gly Ser Ile Cys
305                 310                 315                 320

Gln Tyr Leu Val Met Arg Ala Lys Arg Lys Leu Gly Asp His Leu Pro
            325                 330                 335

Ser Arg Leu Ser Glu Gln Val Glu Leu Arg Arg Ala Gln Ser Leu Pro
        340                 345                 350

Ser Val Pro Leu Ser Cys Ala Thr Tyr Ser Glu Ala Leu Pro Asn Trp
    355                 360                 365

Val Arg Asn Asn Leu Ser Leu Gly Asp Ala Leu Ala Lys Trp Glu Glu
370                 375                 380

Cys Gln Arg Gln Leu Leu Leu Gly Leu Phe Cys Thr Asn Val Ala Phe
385                 390                 395                 400

Pro Pro Asp Ala Leu Arg Met Arg Ala Pro Ala Ser Pro Thr Ala Ala
            405                 410                 415

Asp Pro Ala Thr Pro Gln Asp Pro Pro Gly Leu Pro Pro Cys
        420                 425                 430

<210> SEQ ID NO 4
<211> LENGTH: 1799
<212> TYPE: DNA
<213> ORGANISM: Mus musculus

<400> SEQUENCE: 4
acagcgtctc cgcctccgcc ggcggagacc ccaaggtatc gagactgcgg gacccactgc    60
ccgcaggaca tcgagtcacg atgttcacga gggagaccaa gtggaacatc tcattcgctg   120
gctgcggctt cctcggggtc taccacattg cgtggcctc ctgcctccgt gagcacgcgc   180
ccttcctggt ggccaacgcc actcacatct acggagcctc ggcaggggcg ctcaccgcca   240
cagcgctggt cactggggcc tgcctgggtg aagcaggtgc caacattatt gaggtgtcca   300
aggaggcccg gaagcggttc ctgggtcctc tgcatccctc cttcaacctg gtgaagacca   360
tccgtggctg tctactaaag accctgcctg ctgattgcca tgagcgcgcc aatggacgcc   420
tgggcatctc cctgactcgt gtttcagacg gagagaacgt catcatatcc cactttagct   480

```
ccaaggatga gctcatccag gccaatgtct gcagcacatt tatcccggtg tactgtggcc      540
tcattcctcc tacccctccaa ggggtgcgct atgtggatgg cggcatttca gacaacttgc    600
cactttatga gctgaagaat accatcacag tgtccccatt ctcaggcgag agtgacatct    660
gccctcagga cagctccacc aacatccacg agcttcgcgt caccaacacc agcatccagt    720
tcaaccttcg caatctctac cgcctctcga aggctctctt cccgccagag cccatggtcc    780
tccgagagat gtgcaaacag ggctacagag atggacttcg attccttagg aggaatgccc    840
tgctggaggc ctgtgtggaa ccaaaggacc tgatgaccac cctttccaac atgctaccag    900
tgcgcctggc aacggccatg atggtgccct atactctgcc gctggagagt gcagtgtcct    960
tcaccatccg cttgttggag tggctgcctg atgtccctga agatatccgg tggatgaaag    1020
agcagacggg tagcatctgc cagtatctgg tgatgagggc caagaggaaa ttgggtgacc    1080
atctgccttc cagactgtct gagcaggtgg aactgcgacg tgcccagtct ctgccctctg    1140
tgccactgtc ttgcgccacc tacagtgagg ccctacccaa ctgggtacga aacaacctct    1200
cactggggga cgcgctggcc aagtgggaag aatgccagcg tcagctactg ctgggtctct    1260
tctgcaccaa tgtggccttc ccgccggatg ccttgcgcat gcgcgcacct gccagcccca    1320
ctgccgcaga tcctgccacc ccacaggatc cacctggcct cccgccttgc tgagaatcac    1380
cattcccaca tcgcccggct accagccaag ctccaagttg tcctgcccca ctaagaggag    1440 cccgggtg aacaagatc ctgtctgccc cggctctccc ccttacatgc tgtggaatga    1500
ggacatagga ccctgcacag ctgcaagtgg gctttcgatg tgaaaccttt caccagccac    1560
tcactatgct actcctggtg gggagggatg gggagtcgcc ctcccccgga gcccacagag    1620
ccctcccccg tcacgtcacc tgtgccttac tcctgcccac cacctttca gtgcagggtc      1680 agtcttaaga actccacatc tgctgctgct ccctggtgtc caagtttcct tgcagagtgt    1740
gtgaagaatt atttatttt gccaaagcag atctaataaa agccacagct cagcttctg     1799
```

<210> SEQ ID NO 5
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 5
tggtaccgtt cccgagggag accaagtgga                                      30

<210> SEQ ID NO 6
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 6
cctcgagcgc aaggcgggag gccaggt                                         27

<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 7
tggtacctat ggatttacgc agatgacaca                                      30

```
<210> SEQ ID NO 8
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 8
cctcgagcgt tcagtggtgc agcaggcg                                          28

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tggaacatct cattcgctgg                                                   20

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
aatgccgcca tccacatag                                                    19
```